US00RE49851E

(19) United States
(12) Reissued Patent
Luo et al.

(10) Patent Number: US RE49,851 E
(45) **Date of Reissued Patent: *Feb. 27, 2024**

(54) PYRIDINYLAMINOPYRIMIDINE DERIVATIVES, PREPARATION PROCESS AND USE THEREOF

(71) Applicant: Shanghai Allist Pharmaceuticals Co., Ltd., Shanghai (CN)

(72) Inventors: Huibing Luo, Shanghai (CN); Huayong Zhou, Shanghai (CN); Shuhui Wang, Shanghai (CN); Yong Wu, Shanghai (CN)

(73) Assignee: Shanghai Allist Pharmaceuticals Co., Ltd., Shanghai (CN)

( * ) Notice: This patent is subject to a terminal disclaimer.

(21) Appl. No.: 17/376,987

(22) Filed: Jul. 15, 2021

Related U.S. Patent Documents

Reissue of:
(64) Patent No.: 10,072,002
Issued: Sep. 11, 2018
Appl. No.: 15/329,044
PCT Filed: Jul. 29, 2015
PCT No.: PCT/CN2015/000540
§ 371 (c)(1),
(2) Date: Jan. 25, 2017
PCT Pub. No.: WO2016/015453
PCT Pub. Date: Apr. 2, 2016

U.S. Applications:
(63) Continuation of application No. 16/517,790, filed on Jul. 22, 2019, now Pat. No. Re. 48,687, which is an application for the reissue of Pat. No. 10,072,002, filed as application No. PCT/CN2015/000540 on Jul. 29, 2015.

(30) Foreign Application Priority Data

Jul. 29, 2014 (CN) ..... 201410365911.4

(51) Int. Cl.
*C07D 471/04* (2006.01)
*A61K 31/506* (2006.01)
*C07D 401/14* (2006.01)
*C07D 403/14* (2006.01)

(52) U.S. Cl.
CPC ..... *C07D 471/04* (2013.01); *A61K 31/506* (2013.01); *C07D 401/14* (2013.01); *C07D 403/14* (2013.01)

(58) Field of Classification Search
CPC .. C07D 471/04; C07D 401/14; C07D 403/14; A61K 31/506; A61K 31/404; A61K 31/444; A61P 35/00; A61P 35/02; A61P 43/00
See application file for complete search history.

(56) References Cited

U.S. PATENT DOCUMENTS

| | | | | |
|---|---|---|---|---|
| 8,946,235 | B2 | 2/2015 | Butterworth et al. | |
| 10,472,349 | B2 | 11/2019 | Luo et al. | |
| 10,550,101 | B2 | 2/2020 | Luo et al. | |
| RE48,687 | E * | 8/2021 | Luo ..... | A61K 31/506 |
| 2013/0053409 | A1 | 2/2013 | Butterworth et al. | |

FOREIGN PATENT DOCUMENTS

| | | | |
|---|---|---|---|
| CN | 102482277 | A | 5/2012 |
| CN | 103702990 | A | 4/2014 |
| CN | 104761544 | A | 7/2015 |
| WO | 2012061299 | A1 | 5/2012 |
| WO | WO 2012/061299 | A1 | 5/2012 |
| WO | 2013014448 | A1 | 1/2013 |
| WO | WO 2013/014448 | A1 | 1/2013 |
| WO | 2015188777 | A1 | 12/2015 |

OTHER PUBLICATIONS

Reddi et al, "Mutations in the EGFR Pathway," Clinical Laboratory New, Oct. 1, 2013, pp. 1-9. (Year: 2013).*
Thomas et al, "Rethink of EGFR in Cancer With Its Kinase Independent Function on Board," Front Oncol., 2019 9:800. (Year: 2019).*
Shi et al, "Emerging strategies to overcome resistance to third-generation EGFR inhibitors," Journal of Hematology & Oncology, 2022, 15:94. (Year: 2022).*
"Chinese Office Action corresponding to Chinese Application No. 201410365911.4 dated Jul. 25, 2017".
"Office Action corresponding to Japanese Patent Application No. 2017-504644 dated Mar. 13, 2018".
(Continued)

*Primary Examiner* — Alan D Diamond
(74) *Attorney, Agent, or Firm* — Myers Bigel, P.A.

(57) ABSTRACT

The present invention relates to pyridinylaminopyrimidine derivatives represented by the following formula (I), and pharmaceutically acceptable salts, preparation process and use thereof, wherein $R_1$, $R_2$, $R_3$, $R_4$, $R_5$, m and A are defined as in the description. Pyridinylaminopyrimidine derivatives of the present invention can selectively inhibit the activity of mutant-type epidermal growth factor receptor (EGFR), have a good inhibition for the cancer cell proliferation, and therefore can be used as a therapeutic agent for treating tumors and relevant diseases.

(I)

4 Claims, 1 Drawing Sheet

(56) References Cited

OTHER PUBLICATIONS

Besse, et al., ""Neratinib (HKI-272), an irreversible pan-ErbB receptor tyrosine kinase inhibitor: preliminary results of a phase 2 trial in patients with advanced non-small cell lung cancer", Poster Session—Phase II 203:64 (2008)".

Janne, ""Multicenter, Randomized, Phase II Trial of CI-1033, an Irreversible Pan-ERBB Inhibitor, for Previously Treated Advanced Non-Small-Cell Lung Cancer", J. Clin. Oneal. 25(25):3936-3944 (2007)".

Katakami, et al., ""LUX-Lung 4: A Phase II Trial of Afatinib in Patients with Advanced Non-Small-Cell Lung Cancer who Progressed During Prior Treatment with Erlotinib, Gefitinib, or Both", J. Clin. Oneal. 31 :3335-3341 (2013)".

Landi, et al., ""Irreversible EGFR-TKIs: dreaming perfection", Transi Lung Cancer Res. 2(1):40-49 (2013)".

Li, et al., ""BIBW2992, an irreversible EGFR/HER2 inhibitor highly effective in preclinical lung cancer models", Oncogene 27:4702-4711 (2008)".

Walter, et al., ""Discovery of a mutant-selective covalent inhibitor of EGFR that overcomes T790M-mediated resistance in NSCLC", Cancer Discov. 3(12):1404-1415 (2013)".

Ward, et al., ""Structure-and-Reactivity-Based Development of Covalent Inhibitors of the Activating and Gatekeeper Mutant Forms of the Epidermal Growth Factor Receptor (EGFR)", Journal of Medicinal Chemistry, American Chemical Society 56(17):7025-7048 (2013)".

Jänne et al. "Phase I Dose-Escalation Study of the Pan-HER Inhibitor, PF299804, in Patients with Advanced Malignant Solid Tumors", *Clin. Cancer Res.* 17:1131-1139 (2011).

Pao et al. "Acquired Resistance of Lung Adenocarcinomas to Gefitinib or Erlotinib is Associated with a Second Mutation in the EGFR Kinase Domain", *PLoS Medicine* 2(3):0225-0235 (2005).

Zhou et al. "Novel mutant-selective EGFR kinase inhibitors against EGFR T790M", *Nature* 462(24):1070-1074 (2009).

International Search Report corresponding to International Application No. PCT/CN2015/000540 dated Oct. 28, 2015.

Office Action corresponding to Canadian Application No. 2,956,628 dated Apr. 25, 2018.

Extended European Search Report corresponding to European Application No. 15828199.8 dated Nov. 29, 2017.

* cited by examiner

PYRIDINYLAMINOPYRIMIDINE DERIVATIVES, PREPARATION PROCESS AND USE THEREOF

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS

This application is a *continuation reissue of U.S. patent application Ser. No. 16/517,790 filed Jul. 22, 2018, which is a reissue application of U.S. patent application Ser. No. 15/329,044 filed Jan. 25, 2017, now U.S. Pat. No. 10,072,002, which is a* 35 U.S.C. § 371 national phase application of and claims priority to PCT Application PCT/CN2015/000540 filed Jul. 29, 2015, which claims priority to Chinese Application No. 201410365911.4 filed Jul. 29, 2014, the entire contents of which are incorporated herein by reference in their entirety.

TECHNICAL FIELD

The present invention relates to pyridinylaminopyrimidine derivatives, which selectively inhibit the activity of mutation-type epidermal growth factor receptor (EGFR), a pharmaceutically acceptable salt thereof, a process for preparing the same, a pharmaceutical composition containing said derivative and a pharmaceutically acceptable salt thereof, uses of said derivative and a pharmaceutically acceptable salt thereof in treating some mutation-type EGFR mediated diseases and in manufacture of a medicament for treating some mutation-type EGFR mediated diseases.

BACKGROUND

Cancer has been considered as a disease of the intracellular signal transconducing system or signal transduction mechanism. The most common cause of cancer is a series of defects, either in proteins, when they are mutated, or in the regulation of the quantities of the proteins in the cells such that they are over or under produced. Mutations to the cell surface receptors, which usually transduce the signals into the cells by means of tyrosine kinases, can lead to activation of the kinase in the absence of ligand, and passing of a signal which does not really exist. Alternatively, many receptor tyrosine kinases can be overexpressed on the cell surface leading to an inappropriately strong response to a weak signal.

Epidermal cell growth factors receptors (EGFR) are identified as one significant driving factor in the process for cellular growth and proliferation. The epidermal cell growth factors receptors family is composed of EGFR (Erb-B1), Erb-B2 (HER-2/neu), Erb-B3 and Erb-B4. The epidermal cell growth factors receptors are concerned in the process for most cancers, such as lung cancer, colon cancer and breast cancer. The overexpression and mutation of EGFR have been proved to be the leading risk factor for a breast cancer with poor prognosis. Besides, it has been verified that each of the above four members of the receptors family can aggregate with another member into a heterodimer, and form a signal transduction complex. Overexpression of one or more member(s) of this family in a malignant tumor will result in a synergistic signal transduction.

EGFR belongs to the protein tyrosine kinase (PTK) family. The protein tyrosine kinase is an group of enzymes which catalyze the transportation of phosphate groups from adenosine triphosphate (ATP) to the tyrosine residue located in a protein substrate. Protein tyrosine kinases function in normal cell growth. The overexpression and mutation of EGFR may cause the activation of receptors without ligands and the phosphorylation of some proteins, and then the signal for cell division is produced. As a result, EGFR may magnify the weak signal excessively by its own tyrosine-kinase action, and render the overproliferation of cells.

Specific PTK inhibitors as a potential anti-cancer therapeutic drug are of wide concern. Typical representatives of currently market available EGFR reversible inhibitors include Gefitinib, Erlotinib and Lapatinib, and inhibit the EGFR wild-type and activating mutations (e.g. Exon 19 deletion activating mutation, or L858R activating mutation). Their structures are as follows, and are respectively useful for treating non-small cell lung cancer (NSCLC) and breast cancer. Clinical study proves gefitinib and erlotinib have a favorable therapeutic effect on NSCLC patients with EGFR exon 19 deletion or L858R mutation. However, their limitations are that patients develop drug resistance after treatment, so that inhibitors of this type are limited in their further clinical applications. The study shows that 50% of resistance formed after the treatment with gefitinib and erlotinib is associated with a second mutation occurred in EGFR (T790M) (Pao W. et al., Plos Med., 2:1-11, 2005). The therapeutic effect as reversible inhibitor is lost.

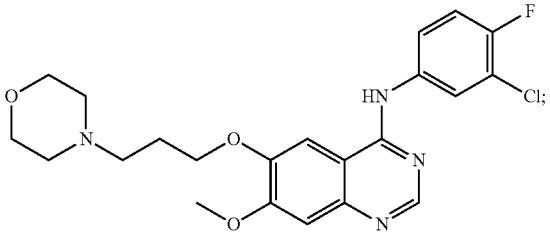

gefitinib

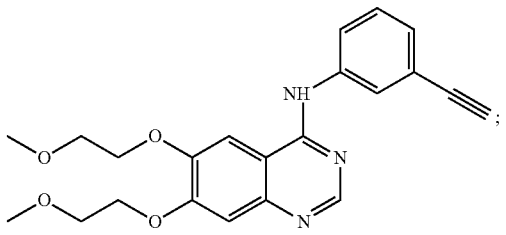

erlotinib

-continued

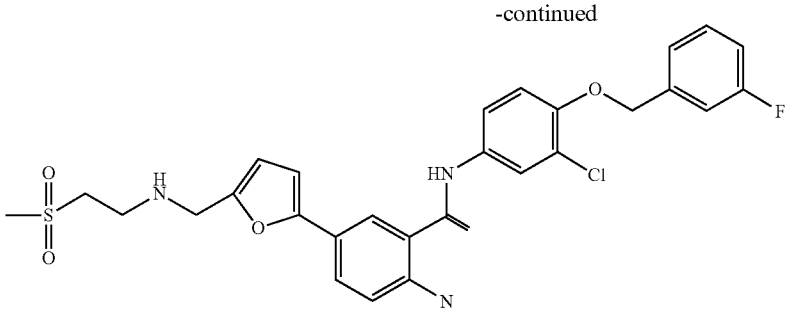

lapatinib

T790M is located at the entrance of the ATP binding pocket of EGFR, and the size of its side chain directly affects the ability of EGFR binding to ATP. The T790M mutation spatially inhibits the interaction of the EGFR inhibitor and the ATP binding site, increases the affinity of EGFR to ATP, and makes the cells resistant to the EGFR inhibitors.

Compared to reversible EGFR inhibitors, irreversible EGFR inhibitors have very prominent advantages. Irreversible EGFR inhibitors can inhibit EGFR for a long time and are only limited by the normal rate of receptor re-binding (also called reversion). It is found that the irreversible EGFR inhibitor can covalently bind to the cysteine residue (Cys797) of the EGFR by Michael addition reaction and expand the binding sites of irreversible EGFR inhibitors and the ATP, so that the resistance caused by the T790M mutation can be overcame to some extent (Li D et al., Oncogenc, 27:4702-4711, 2008). Currently market available irreversible EGFR inhibitors include BIBW-2992 (Afatinib), those in development include HKI-272 (Neratinib), EKB-569 (Pelitinib), PF00299804 (Dacomitinib) and the like, and their structures are as follows.

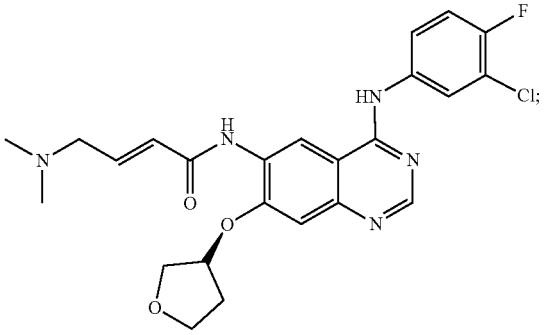

BIBW-2992

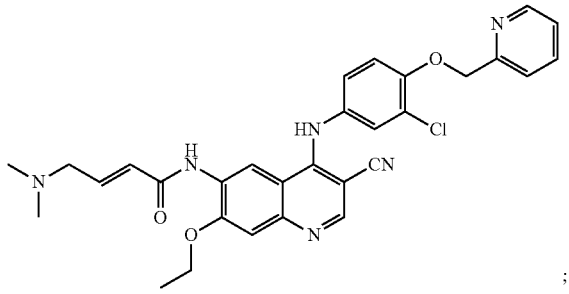

neratinib(HKI-272)

;

-continued

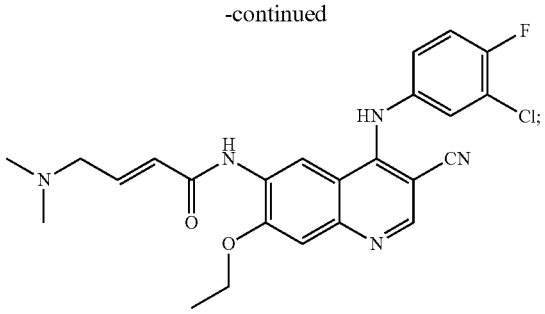

pelitinib(EKB-569)

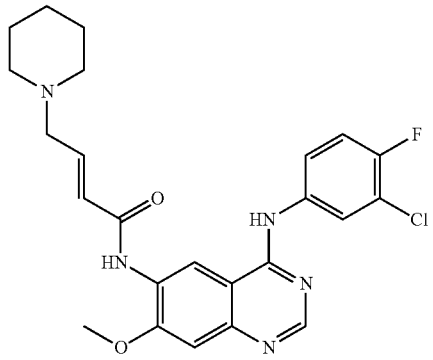

dacomitinib

However, these irreversible EGFR inhibitors, which can inhibit EGFR T790M, also have a large inhibition effect on the wild-type EGFR, leading to severe side effects such as diarrhea, erythra, nausea, anorexia, and weakness (Besse, B. et al. Eur. J. Cancer Suppl., 6, 64, abstr. 203, 2008; Janne, P. A. et al., J. Clin. Oncol., 25: 3936-3944, 2007). Accordingly although it is reported in the literature that in the preclinical study, BIBW2992 (Afatinib) and PF00299804 (Dacomitinib) show a significant antitumor activity and can inhibit the activities of EGFR and EGFR T790M, however, due to the occurrence of these adverse reactions, the clinical dose and the effective blood drug concentration are limited in the clinical course. Therefore, there is no remarkable progress for BIBW2992 (Afatinib) and PF00299804 (Dacomitinib) in overcoming the T790M resistant mutation (Katakami N, Atagi S, Goto K, et al. [J]. Journal of Clinical Oncology, 2013, 31(27): 3335-3341.; Jänne P A, Boss D S, Camidge D R, et al. [J]. Clinical Cancer Research, 2011, 17(5): 1131-1139.; Landi L, Cappuzzo F. [J]. Translational Lung Cancer to Research, 2013, 2(1): 40-49.).

The above-mentioned reversible or irreversible EGFR inhibitors, being currently marketed or under development, are mainly quinazoline compounds. The currently reported quinazoline EGFR inhibitors are the ATP competitive inhibitors of wild-type EGFR, leading to the occurrence of some side-reaction. In 2009, a group of pyrimidine-based irreversible EGFR inhibitors which are specific to the EGFR T790M was reported by the researchers, and the structures are shown below. Compared to the existing aniline quinazoline EGFR inhibitors, these pyrimidine-based compounds have a 30-100 fold higher inhibition activity for the EGFR T790M, and a 100 fold lower inhibition activity for the wild-type EGFR (WenjunZhou et al., Nature, 462:1070-1074, 2009). However, these pyrimidine-based compounds did not enter the clinical study later.

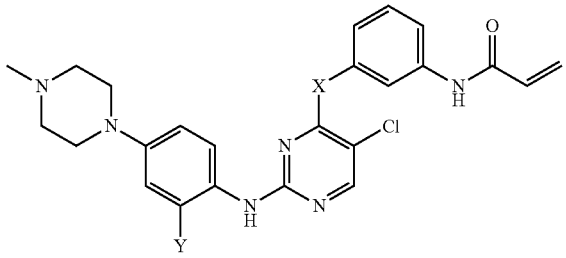

X = O, S
Y = H, OMe

International Patent Application WO 2012/061299 A1 filed by Avila Therapeutics discloses another series of pyrimidine-based compounds, and the structures are shown below. The representative compound is CO1686. It is reported in the literature that CO1686 can selectively act on the EGFR activating mutation and the T790M resistant mutation, but have a weak inhibition effect on the wild-type EGFR (Walter A O, Sjin R T T, Haringsma H J, et al. [J]. Cancer discovery, 2013, 3(12): 1404-1415.). Currently, this compound is ready to enter Phase-II clinical stage.

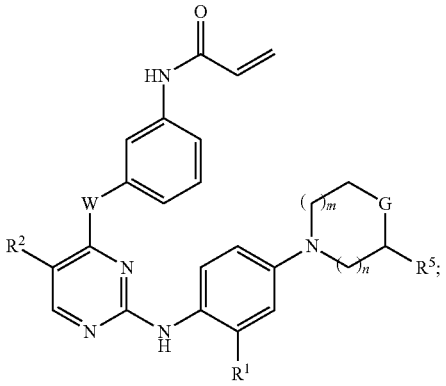

-continued

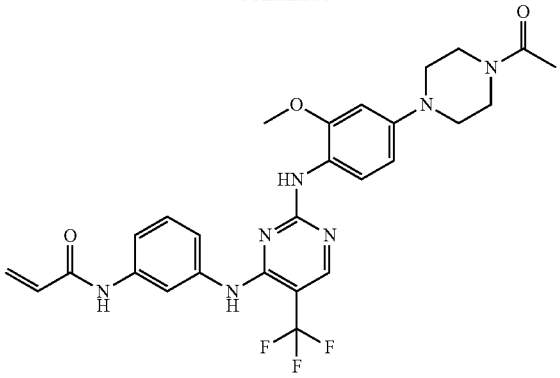

(CO1686)

International Patent Application WO 2013/014448 A1 filed by ASTRAZENECA AB also discloses a series of pyrimidine-based compounds, and their structures are shown below. The representative compound is AZD9291. This compound has a better inhibition effect on the EGFR activating mutation and the T790M resistant mutation than the wild-type EGFR, and is now in Phase I clinical stage.

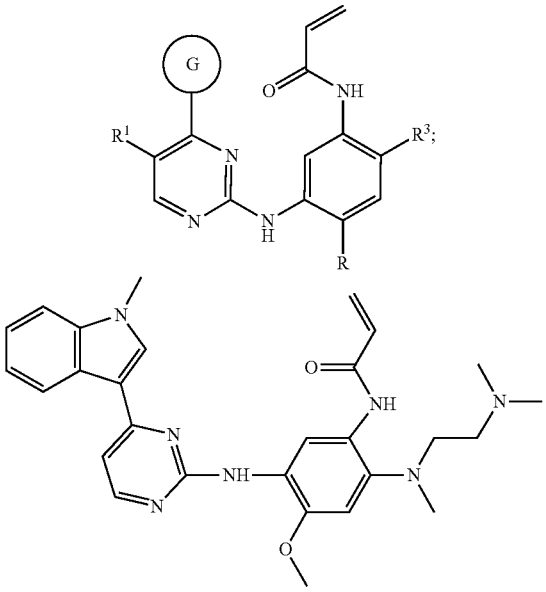

(AZD9291)

There is an urgent demand in the current anti-tumor field to overcome the problems of the clinically common EGFR resistant mutation (e.g. T790M mutation) and the toxic and side effects of the existing EGFR inhibitors, i.e., develop more small molecule inhibitors that show a higher inhibition effect on some activating mutation and resistant mutation EGFRs and a lower inhibition effect on the wild-type EGFR. During the study of the EGFR inhibitors, the present inventors surprisingly discovered a group of pyridinylaminopyrimidine derivatives, which have a remarkably higher inhibition activity on the EGFR activating mutation (e.g. Exon 19 deletion activating mutation, or L858R activating mutation) and the T790M resistant mutation than the wild-type EGFR (WT EGFR), and has good selectivity, low toxic and side effects, and good safety. It is expected that this kind of inhibitors will have a good therapeutic effect, can overcome the problems of drug resistance and toxic/side effects, and accordingly may have good development prospects.

SUMMARY OF THE INVENTION

The present invention provides a compound represented by the following general formula (I), or a pharmaceutically acceptable salt thereof:

(I)

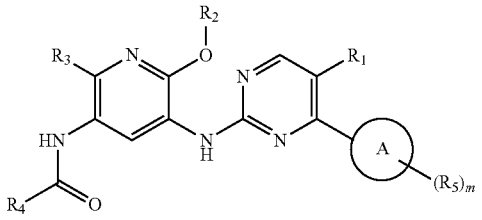

wherein,

Ring A is aryl or heteroaryl;

$R_1$ is selected from a group consisting of hydrogen, halogen, $C_1$-$C_4$alkyl, halo$C_1$-$C_4$-alkyl, $C_2$-$C_6$alkenyl, $C_2$-$C_6$alkynyl or —CN;

$R_2$ is selected from a group consisting of $C_1$-$C_4$alkyl, halo$C_1$-$C_4$-alkyl, $C_2$-$C_6$alkenyl, —$(CH_2)_qOR_7$, —$(CH_2)_qNR_7R_7'$ or —$(CH_2)_qC(O)R_7$;

$R_4$ is 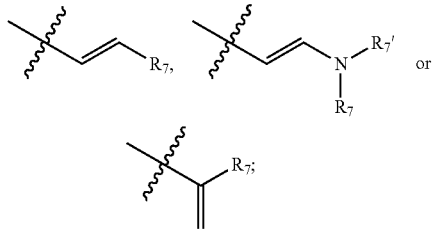 or

Each $R_5$ is [dependently] *independently* halogen, $C_1$-$C_4$alkyl, halo$C_1$-$C_4$alkyl, $C_2$-$C_6$alkenyl, $C_2$-$C_6$alkynyl, —$OR_6$, —$C(O)R_7$, —$C(O)NR_7R_7'$, —$OR_7$, —$NR_7R_7'$, —CN or —$NO_2$;

$R_3$ is selected from a group consisting of halogen, —CN, —$NO_2$, $C_1$-$C_4$alkyl, halo$C_1$-$C_4$alkyl, —$C(O)R_6$, —$C(O)R_7$, —$C(O)NR_7R_7'$, —$OR_7$, —$OR_6$, —$NHR_7$, —$NR_7$-($C_1$-$C_4$alkyl), —$NR_7$-(halo$C_1$-$C_4$alkyl), —$NR_7(CH_2)_nC(O)R_6$, —$NR_6R_7$, —$NR_7$-heterocycloalkyl, wherein said heterocycloalkyl is unsubstituted or substituted with 1-2 substituents selected from $R_7$, or —$NR_7SO_2R_7$, or heterocycloalkyl that is unsubstituted or substituted with 1-3 substituents selected from halogen, $C_1$-$C_4$alkyl, halo$C_1$-$C_4$alkyl, —$(CH_2)_nOH$, —$NR_7R_7'$, —$OR_7$ or —$C(O)R_7$;

wherein, $R_6$ is —$(CH_2)OR_7$, —$(CH_2)_qNR_7R_7'$, —$(CH_2)_qNR_7C(O)R_7$, —$(CH_2)_qC(O)R_7$ or —$(CH_2)_qC(O)NR_7R_7'$;

$R_7$ and $R_7'$ are each independently hydrogen, $C_1$-$C_4$alkyl, $C_2$-$C_6$alkenyl, $C_2$-$C_6$alkynyl or halo$C_1$-$C_4$alkyl, or $R_7$, $R_7'$ and the nitrogen atom attached thereto are cyclized together together to form a heterocycloalkyl that is unsubstituted or substituted with 1-3 substituents selected from halogen, $C_1$-$C_4$alkyl, halo$C_1$-$C_4$alkyl, —$(CH_2)_nOH$, —$NR_7R_7'$, —$OR_7$ or —$C(O)R_7$;

m is 1, 2 or 3;

n is 0, 1, 2, 3 or 4;

q is 0, 1, 2, 3 or 4.

The present invention provides a compound represented by the general formula (I), which can inhibit one or more EGFR activating or resistant mutations, such as L858R activating mutation, Exon 19 deletion activating mutation, and T790M resistant mutation. Advantageously, the present compound can be useful in treating the cancer patient who has been resistant to the existing therapy based on the EGFR inhibitor.

The present invention provides a compound represented by the general formula (I), which shows a higher inhibition to the activating or resistant mutation-type EGFR than the wild-type EGFR. Due to the reduced toxicity associated with the inhibition of the wild-type EGFR, it is therefore expected that the compound of the present invention is more useful as a therapeutic agent, in particular for treating the cancer.

The present invention also provides a process for preparing the compound represented by the general formula (I) of the present invention.

The present invention also provides a pharmaceutical composition, comprising the compound represented by the general formula (I) of the present invention or a pharmaceutically acceptable salt thereof; and a pharmaceutically acceptable carrier, excipient or diluent.

The present invention also provides use of the compound represented by the general formula (I) of the present invention or a pharmaceutically acceptable salt thereof for treating an EGFR activating or resistant mutation-mediated disease, in particular cancer, in mammals, in particular human.

The present invention also provides use of the compound represented by the general formula (I) of the present invention or a pharmaceutically acceptable salt thereof in manufacture of a medicament for treating an EGFR activating or resistant mutation-mediated disease, in particular cancer, in mammals, in particular human.

The present invention also provides a method for treating an EGFR activating or resistant mutation-mediated disease, in particular cancer, in mammals, in particular human, said method comprises administrating to a patient the compound represented by the general formula (I) or a pharmaceutically acceptable salt thereof, or the pharmaceutical composition comprising a therapeutically effective amount of the compound represented by the general formula (I) and a pharmaceutically acceptable carrier, excipient or diluent.

The present invention also provides a method of selectively inhibiting the EGFR activating or resistant mutation over the wild-type EGFR (WT EGFR), said method comprises contacting a biological sample with or administrating to a patient the compound represented by the general formula (I) or a pharmaceutically acceptable salt thereof or a pharmaceutical composition comprising the same.

The cancer as mentioned in the present invention can be selected from a group consisting of lung cancer, ovarian cancer, cervical cancer, breast cancer, stomach cancer, colorectal cancer, pancreatic cancer, glioma, glioblastoma, melanoma, prostate cancer, leukemia, lymphoma, nonHodgkin's lymphoma, hepatocytes cancer, gastrointestinal stromal tumor (GIST), thyroid cancer, cholangiocarcinoma, endometrial cancer, renal cancer, anaplastic large cell lymphoma, acute myeloid leukemia (AML), multiple myeloma, and mesothelioma.

In a preferable embodiment of the compound represented by the general formula (I) or a pharmaceutically acceptable salt thereof according to the present invention, Ring A is heteroaryl.

In a more preferable embodiment of the compound represented by the general formula (I) or a pharmaceutically acceptable salt thereof according to the present invention, Ring A is indolyl, indazolyl, [pyrro] *pyrrolo*[2,3-c]pyridinyl, [pyrro] *pyrrolo*[3,2-c]pyridinyl, [pyrro] *pyrrolo*[2,3-b]pyridinyl, [pyrro] *pyrrolo*[3,2-b]pyridinyl, [pyrro] *pyrrolo*[2,3-b]pyrazinyl, indolin-2-onyl, pyridinyl, pyrazolyl or pyrimidinyl.

In a preferable embodiment of the compound represented by the general formula (I) or a pharmaceutically acceptable salt thereof according to the present invention, $R_1$ is hydrogen, halogen or halo$C_1$-$C_4$alkyl.

In a more preferable embodiment of the compound represented by the general formula (I) or a pharmaceutically acceptable salt thereof according to the present invention, $R_1$ is hydrogen, chloro, fluoro or trifluoromethyl.

In a preferable embodiment of the compound represented by the general formula (I) or a pharmaceutically acceptable salt thereof according to the present invention, $R_2$ is $C_1$-$C_4$alkyl or halo$C_1$-$C_4$alkyl, preferably $C_2$-$C_4$alkyl or halo$C_2$-$C_4$alkyl, more preferably isopropyl or trifluoroethyl.

In a preferable embodiment of the compound represented by the general formula (I) or a pharmaceutically acceptable salt thereof according to the present invention, $R_4$ is

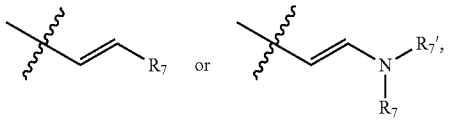

$R_7$ and $R_7$' are each independently hydrogen or $C_1$-$C_4$alkyl.

In a more preferable embodiment of the compound represented by the general formula (I) or a pharmaceutically acceptable salt thereof according to the present invention, $R_4$ is

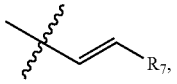

$R_7$ is hydrogen.

In a preferable embodiment of the compound represented by the general formula (I) or a pharmaceutically acceptable as salt thereof according to the present invention, $R_3$ is selected from a group consisting of halogen, —CN, —$NO_2$, $C_1$-$C_4$alkyl, halo$C_1$-$C_4$alkyl, —C(O)$R_7$, —C(O)$NR_7R_7$', —O$R_7$, —NH$R_7$, —N$R_7$—($C_1$-$C_4$alkyl), —N$R_7$($CH_2$)$_n$C(O)$R_6$ or —N$R_6R_7$, or heterocycloalkyl that is unsubstituted or substituted with 1-3 substituents selected from halogen, $C_1$-$C_4$alkyl, halo$C_1$-$C_4$alkyl, —($CH_2$)$_n$OH, —N$R_7R_7$', —O$R_7$ or —C(O)$R_7$;

wherein, $R_6$ is —($CH_2$)$_q$O$R_7$, —($CH_2$)$_q$N$R_7R_7$', —($CH_2$)$_q$C(O)$R_7$ or —($CH_2$)$_q$C(O)N$R_7R_7$';

$R_7$ and $R_7$' are each independently hydrogen, $C_1$-$C_4$alkyl or halo$C_1$-$C_4$alkyl, or $R_7$, $R_7$' and the nitrogen atom attached thereto are cyclized together to form a heterocycloalkyl;

n is 0, 1, 2, 3 or 4;

q is 0, 1, 2, 3 or 4.

In a more preferable embodiment of the compound represented by the general formula (I) or a pharmaceutically acceptable salt thereof according to the present invention, $R_3$ is —N$R_6R_7$, wherein $R_6$ is —($CH_2$)$_q$N$R_7R_7$', $R_7$ and $R_7$' are each independently hydrogen or $C_1$-$C_4$alkyl, q is 2.

In a more preferable embodiment of the compound represented by the general formula (I) or a pharmaceutically acceptable salt thereof according to the present invention, $R_3$ is a heterocycloalkyl substituted by one substituent selected from halogen, $C_1$-$C_4$alkyl, halo$C_1$-$C_4$alkyl or —N$R_7R_7$', $R_7$ and $R_7$' are each independently hydrogen or $C_1$-$C_4$alkyl; more preferably, the heterocycloalkyl is pyrrolidinyl.

In a preferable embodiment of the compound represented by the general formula (I) or a pharmaceutically acceptable salt thereof according to the present invention, each $R_5$ is [dependently] *independently* halogen, $C_1$-$C_4$alkyl, halo$C_1$-$C_4$alkyl, —O$R_7$, —N$R_7R_7$', —CN or —$NO_2$, $R_7$ and $R_7$' are each independently hydrogen or $C_1$-$C_4$alkyl, m is 1, 2 or 3.

In a more preferable embodiment of the compound represented by the general formula (I) or a pharmaceutically acceptable salt thereof according to the present invention, each $R_5$ is [dependently] *independently* halogen, $C_1$-$C_4$alkyl, —O$R_7$ or —N$R_7R_7$', $R_7$ and $R_7$' are each independently hydrogen or $C_1$-$C_4$alkyl, m is 1, 2 or 3.

The specifically preferable compound represented by the general formula (I) or a pharmaceutically acceptable salt thereof according to the present invention includes:

N-{2-{[2-(dimethylamino)ethyl](methyl)amino}-6-isopropyloxy-5-{5-chloro-[4-(1-methyl-1H-indol-3-yl)pyrimidin-2-yl]amino}pyridin-3-yl}acrylamide;

N-{2-{[2-(dimethylamino)ethyl](methyl)amino}-6-isopropyloxy-5-{[4-(1-methyl-1H-indol-3-yl)pyrimidin2-yl]amino}pyridin-3-yl}acrylamide;

N-{2-{[2-(dimethylamino)ethyl](methyl)amino}-6-(2,2,2-trifluoroethoxyl)-5-{[4-(1-methyl-1H-indol-3-yl)pyrimidin-2-yl]amino}pyridin-3-yl}acrylamide;

N-{2-{[2-(dimethylamino)ethyl](methyl)amino}-6-(2,2,2-trifluoroethoxyl)-5-{5-chloro-[4-(1-methyl-1H-indol-3-yl)pyrimidin-2-yl]amino}pyridin-3-yl}acrylamide;

N-{2-{[2-(dimethylamino)ethyl](methyl)amino}-6-isopropyloxy-5-{[4-(1-methyl-5-fluoro-1H-indol-3-yl)pyrimidin-2-yl]amino}pyridin-3-yl}acrylamide;

N-{2-{[2-(dimethylamino)ethyl](methyl)amino}-6-isopropyloxy-5-{[4-(1-methyl-5,6-difluoro-1H-indol-3-yl)pyrimidin-2-yl]amino}pyridin-3-yl}acrylamide;

N-{2-{[2-(dimethylamino)ethyl](methyl)amino}-6-isopropyloxy-5-{5-chloro[4-(1-methyl-6-fluoro-1H-indol-3-yl)pyrimidin-2-yl]amino}pyridin-3-yl}acrylamide;

N-{2-{[2-(dimethylamino)ethyl](methyl)amino}-6-isopropyloxy-5-{5-chloro[4-(1-methyl-5,6-difluoro-1H-indol-3-yl)pyrimidin-2-yl]amino}pyridin-3-yl}acrylamide;

N-{2-{[2-(dimethylamino)ethyl](methyl)amino}-6-isopropyloxy-5-{5-chloro-[4-(1-methyl-5-fluoro-1H-indol-3-yl)pyrimidin-2-yl]amino}pyridin-3-yl}acrylamide;

N-{2-{[2-(dimethylamino)ethyl](methyl)amino}-6-isopropyloxy-5-{5-fluoro-[4-(1-methyl-5-fluoro-1H-indol-3-yl)pyrimidin-2-yl]amino}pyridin-3-yl}acrylamide;

N-{2-{[2-(dimethylamino)ethyl](methyl)amino}-6-isopropyloxy-5-{5-fluoro-[4-(1-methyl-1H-indol-3-yl)pyrimidin-2-yl]amino}pyridin-3-yl}acrylamide;

N-{2-{[2-(dimethylamino)ethyl](methyl)amino}-6-isopropyloxy-5-{5-fluoro[4-(1-methyl-5,6-difluoro-1H-indol-3-yl)pyrimidin-2-yl]amino}pyridin-3-yl}acrylamide;

N-{2-{[2-(dimethylamino)ethyl](methyl)amino}-6-isopropyloxy-5-{[4-(1-methyl-6-fluoro-1H-indol-3-yl)pyrimidin-2-yl]amino}pyridin-3-yl}acrylamide;

N-{2-{[2-(dimethylamino)ethyl](methyl)amino}-6-(2,2,2-trifluoroethoxyl)-5-{5-fluoro-[4-(1-methyl-1H-indol-3-yl)pyrimidin-2-yl]amino}pyridin-3-yl}acrylamide;

N-{2-{[2-(dimethylamino)ethyl](methyl)amino}-6-(2,2,2-trifluoroethoxyl)-5-{[4-(1-methyl-5-fluoro-1H-indol-3-yl)pyrimidin-2-yl]amino}pyridin-3-yl}acrylamide;

N-{2-{[2-(dimethylamino)ethyl](methyl)amino}-6-isopropyloxy-5-{5-chloro-[4-(1-methyl-1H-indol-3-yl)pyrimidin-2-yl]amino}pyridin-3-yl}acrylamide methanesulfonate;

N-{2-{[2-(dimethylamino)ethyl](methyl)amino}-6-isopropyloxy-5-{5-chloro-[4-(1-methyl-5,6-difluoro-1H-indol-3-yl)pyrimidin-2-yl]amino}pyridin-3-yl}acrylamide methanesulfonate;

N-{2-{[2-(dimethylamino)ethyl](methyl)amino}-6-isopropyloxy-5-{[4-(1-methyl-5,6-difluoro-1H-indol-3-yl)pyrimidin-2-yl]amino}pyridin-3-yl}acrylamide methanesulfonate;

N-{2-{[2-(dimethylamino)ethyl](methyl)amino}-6-isopropyloxy-5-{[5-chloro-4-(1-methyl-1H-[pyrro]*pyrrolo*[2,3-b]pyridin-3-yl)pyrimidin-2-yl]amino}pyridin-3-yl}acrylamide;

N-{2-{[2-(dimethylamino)ethyl](methyl)amino}-6-isopropyloxy-5-{[5-chloro-4-(1-methyl-1H-[pyrro]*pyrrolo*[2,3-b]pyridin-5-yl)pyrimidin-2-yl]amino}pyridin-3-yl}acrylamide;

N-{2-{[2-(dimethylamino)ethyl](methyl)amino}-6-isopropyloxy-5-{[5-chloro-4-(1-methyl-1H-pyrazol-4-yl)pyrimidin-2-yl]amino}pyridin-3-yl}acrylamide;

N-{2-{[2-(dimethylamino)ethyl](methy)amino}-6-isopropyloxy-5-{[5-chloro-2'-methoxy-(4,5'-bipyrimidine)-2-yl]amino}pyridin-3-yl}acrylamide; and N-{2-{[2-(dimethylamino)ethyl](methyl)amino}-6-isopropyloxy-5-{[5-chloro-2'amino-(4,5'-bipyrimidine)-2-yl]amino}pyridin-3-yl}acrylamide.

The present invention also provides a process for preparing the compound represented by the general formula (I), which comprises the steps of:

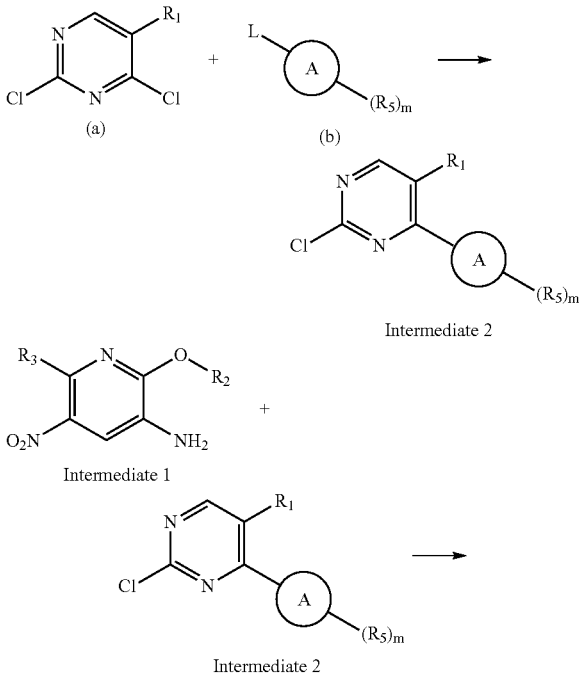

-continued

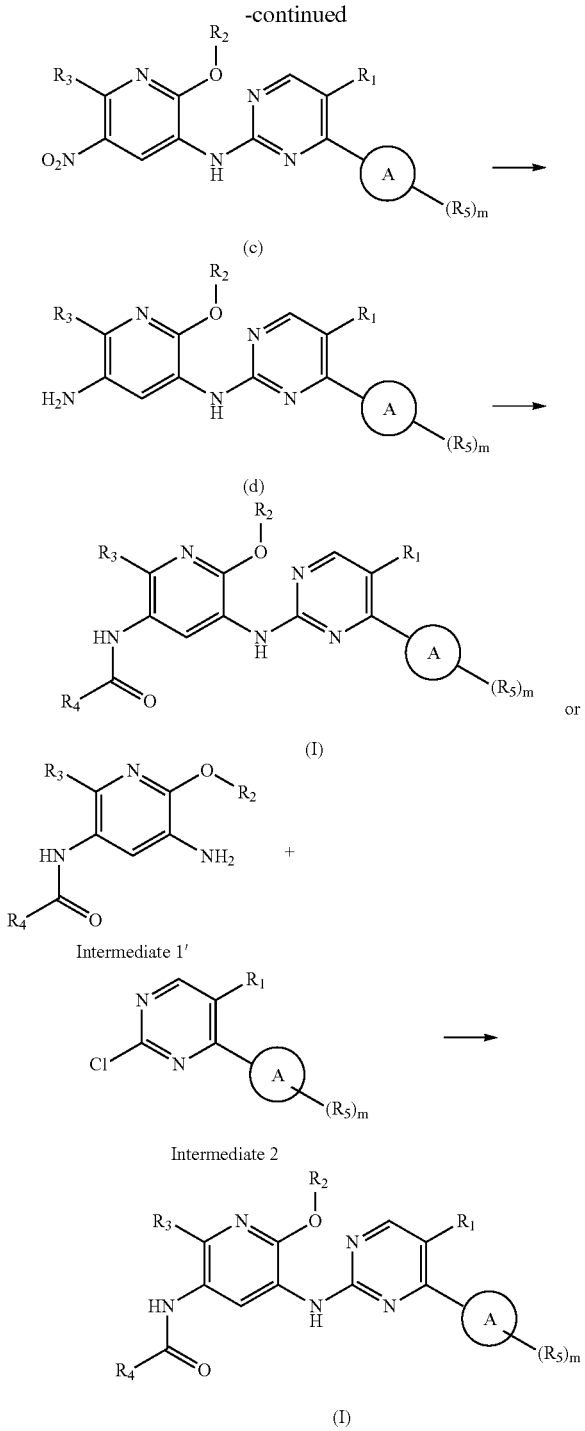

wherein ring A, $R_1$, $R_2$, $R_3$, $R_4$, $R_5$, and m are identical to those defined in the above general formula (I); L represents a leaving group, including hydrogen, halogen or

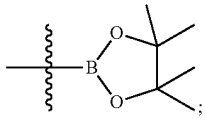

compounds (a) and (b) are used as starting material, and subjected to substitution under a catalyst to produce an Intermediate 2; the Intermediate 2 and an Intermediate 1 are subjected to substitution or coupling reaction to produce a compound (c), the nitro group of the compound (c) is reduced to produce a compound (d), the compound (d) is acylated to produce a compound (I); or the Intermediate 2 and an Intermediate 1' are subjected to substitution or coupling reaction to directly produce a compound (I).

In the process for preparing the compound of the general formula (I), the catalyst for carrying out the substitution reaction of the compounds (a) and (b) includes a Lewis acid such as $AlCl_3$ or a transition metal catalyst such as bis (pinacolato)diboron/$PdCl_2$(dppf), $PdCl_2$(dppf); the substitution or coupling reaction of Intermediate 2 and Intermediate 1 can also be carried out under the catalysis of a transition metal catalyst including but not limited to Pd2(dba)3/xantphos; conventional reducing agents well known in the art are used in the reduction of the nitro group, includes but is not limited to iron powders, zinc powders, sodium sulfide, $H_2/PtO_2$; the acylation of the compound (d) is carried out with the corresponding acyl halide such as acyl chloride.

In an embodiment of preparing the compound represented by the general formula (I) according to the present invention, if Intermediate 2 is Intermediate 2j, the preparation process is as follows,

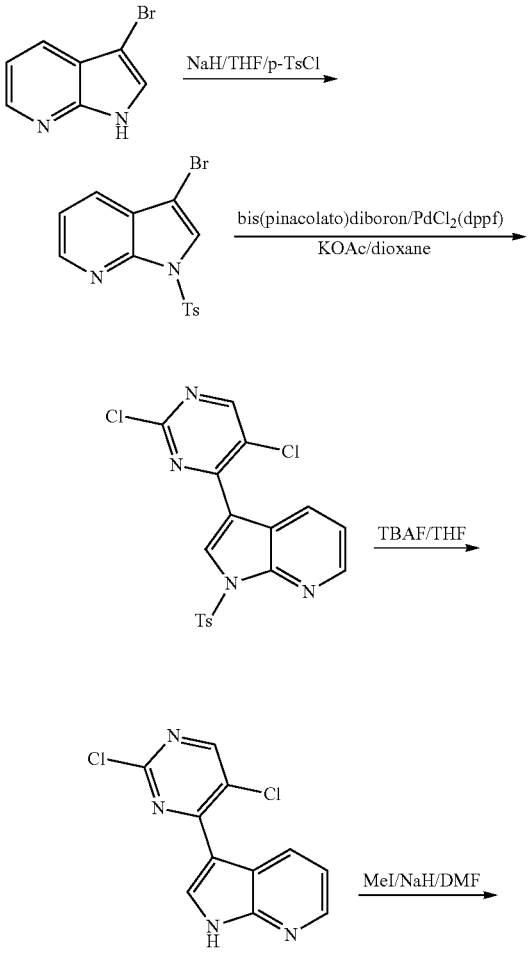

-continued

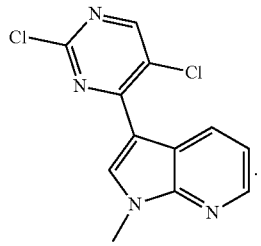

Intermediate 2j

In the process for preparing the compound represented by the general formula (I) according to the present invention, the preparation process for Intermediate 1 and Intermediate 1' comprises the steps of,

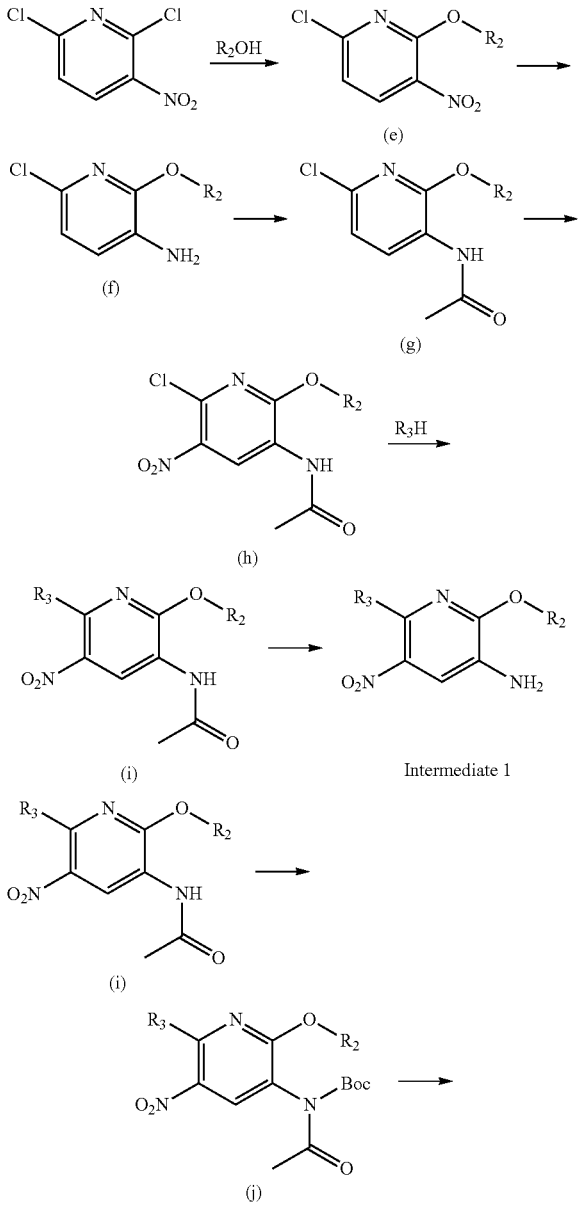

-continued

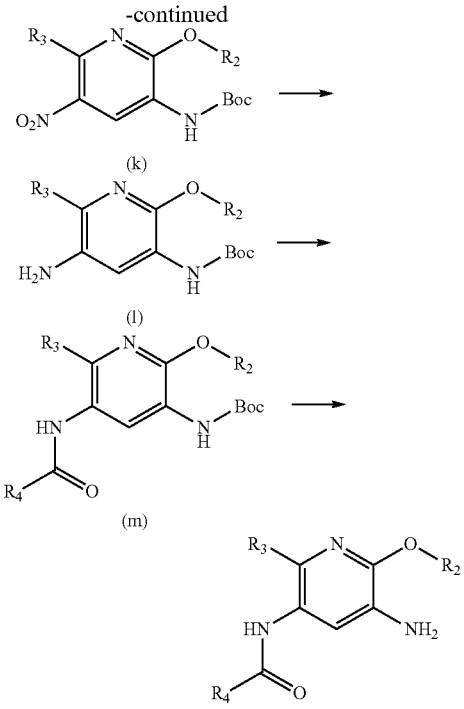

wherein, $R_2$, $R_3$ and $R_4$ are defined as in the above general formula (I); 2,6-dichloro-3-nitropyridine is used as starting material, and subjected to etherification to produce a compound (e), the nitro group of the compound (e) is reduced to produce a compound (f), the compound (f) is then subjected to a reaction to produce a compound (g), the compound (g) is subjected to nitration to produce a compound (h), the compound (h) and $R_3H$ are subjected to substitution to produce a compound (i), and the compound (i) is then deprotected to produce the Intermediate 1; the compound (i) is subjected to Boc-protection to produce a compound (j), the compound (j) is then subjected to acetyl-deprotection to produce a compound (k), the nitro group of the compound (k) is reduced to produce a compound (l), the compound (l) is subjected to acylation to produce a compound (m), and finally the compound (m) is subjected to Boc-deprotection to produce the Intermediate 1'.

In the process for preparing Intermediate 1 and Intermediate 1' according to the present invention, the etherification reaction is carried out in presence of a strong base which includes, but is not limited to sodium hydride, potassium hydride, sodium hydroxide, potassium hydroxide, sodium ethoxide, and sodium methoxide; conventional reducing agents well known in the art are used in the reduction of the nitro group, includes but is not limited to iron powders, zinc powders, sodium sulfide, $H_2/PtO_2$; protection and deprotection are the conventional method well known in the art, and are carried out in an appropriate acidic or basic condition. In the above preparation processes, the used abbreviations for the agents have the following meanings:

| | |
|---|---|
| $AlCl_3$ | Aluminium chloride |
| Bis(pinacolato)diboron | Bis(pinacolato)diboron |
| $PdCl_2$(dppf) | [1,1'-Bis(diphenylphosphino)ferrocene]dichloropalladium |
| $Pd_2(dba)_3$ | Tris(dibenzylideneacetone)dipalladium |

-continued

| | |
|---|---|
| Xantphos | 4,5-Bis(diphenylphosphino)-9,9-dimethylxanthene |
| $PtO_2$ | Platinum dioxide |
| NaH | Sodium hydride |
| THF | tetrahydrofuran |
| p-TsCl | p-Toluenesulfonyl chloride |
| KOAc | Potassium acetate |
| Dioxane | Dioxane |
| $Na_2CO_3$ | Sodium carbonate |
| TBAF | Tetrabutylammonium fluoride |
| MeI | Methyl iodide |
| DMF | N,N-dimethylformamide |

In the present invention, the term "halogen" means fluoro, chloro, bromo iodo and the like, preferably fluoro, chloro and bromo, and more preferably chloro.

In the present invention, the term "$C_1$-$C_4$alkyl" means methyl, ethyl, propyl, isopropyl, butyl, iso-butyl, sec-butyl or tert-butyl, the term "$C_2$-$C_4$alkyl" means ethyl, propyl, isopropyl, butyl, iso-butyl, sec-butyl or tert-butyl, preferably ethyl, propyl, isopropyl or butyl, more preferably isopropyl.

In the present invention, the term "halo$C_1$-$C_4$alkyl" means the $C_1$-$C_4$alkyl, as defined herein, which is substituted with one or more halogen atoms, preferably 1-5 halogen atoms, including but not limited to, trifluoromethyl, trifluoroethyl, difluoromethyl, 1-chloro-2-fluoroethyl and the like. The term "halo$C_2$-$C_4$alkyl" includes but is not limited to trifluoroethyl, difluoromethyl, 1-chloro-2-fluoroethyl and the like, preferably trifluoroethyl.

In the present invention, the term "alkenyl" means a mono-valent group derived from a hydrocarbon group, the term "$C_2$-$C_6$alkenyl" means an alkenyl group containing 2 to 6 carbon atoms and at least containing one C—C double bond, including but not limited to, ethenyl, propenyl, butenyl, 2-methyl-2-butenyl, 2-methyl-2-pentenyl and the like.

In the present invention, the term "alkynyl" means a mono-valent group derived from a hydrocarbon group, the term "$C_2$-$C_6$alkynyl" means an alkynyl group containing 2 to 6 carbon atoms and at least containing one C—C triple bond, including but not limited to, ethynyl, propynyl, 1-butynyl, 2-butynyl and the like.

In the present invention, the term "cycloalkyl" means a mono-valent group derived from monocyclic or polycyclic, saturated or partially unsaturated aliphatic carbocyclic compounds, the term "$C_3$-$C_8$-cycloalkyl" includes but is not limited to cyclopropyl, cyclobutyl, cyclopentyl, cyclohexyl, cycloheptyl, cyclooctyl, cyclooctenyl, cyclopropenyl, cyclobutenyl, cyclopentenyl, cyclohexenyl, cycloheptenyl, and the term "$C_9$-$C_{12}$-" includes but is not limited to bicyclo[2.2.1]heptyl, bicyclo[2.2.1]octyl and the like.

In the present invention, the term "heterocycloalkyl" means a monovalent monocyclic group, which is saturated or partially unsaturated (but not aromatic) and contains 3-8 ring members, preferably 4-7 ring members, or a monovalent fused bicyclic group, which is saturated or partially unsaturated (but not aromatic) and contains 5-12 ring members, preferably 7-10 ring members, wherein 1-4 ring heteroatom(s) is/are selected from a group consisting of O, S and N, and the remaining ring atoms are carbon. Said heterocycloalkyl includes but is not limited to azetidinyl, oxetanyl, pyrrolidinyl, piperidyl, morpholinyl, piperazinyl, tetrahydropyranyl, pyrazolidinyl, pyrazolinyl, imidazolinyl, imidazolidinyl, [1,3]dioxolane (dioxolane), dihydropyridinyl, tetrahydropyridinyl, hexahydropyridinyl, oxazolinyl, oxazolidinyl, iso-oxazolidinyl, thiazolinyl, thiazolidinyl, tetrahydrothiazolyl, iso-tetrahydrothiazolyl, octahydroindolyl, octahydroisoindolyl, tetrahydrofuryl and the like, preferably azetidinyl, oxetanyl, pyrrolidinyl, piperidyl, morpholinyl or piperazinyl.

In the present invention, the term "aryl" means an aromatic cyclic hydrocarbyl, which is a fused or non-fused carbonaceous ring system containing one or more aromatic rings, and includes but is not limited to phenyl, naphthyl, tetrahydronaphthyl, indanyl, indenyl and the like, preferably an aryl containing 6-14 carbon atoms, more preferably an to aryl containing 6-10 carbon atoms, such as phenyl and naphthyl, more preferably phenyl.

In the present invention, the term "heteroaryl" means 5-6 membered monocyclic heteroaryl containing 1-4 heteroatoms selected from N, S or O, or bicyclic heteroaryl formed is by fusing said 5-6 membered monocyclic heteroaryl with a benzene ring, pyridine ring or pyrrole ring, said heteroaryl can be partially saturated. Said heteroaryl includes but is not limited to furyl, thienyl, pyrrolyl, imidazolyl, pyrazolyl, thiazolyl, isothiazolyl, oxazolyl, isoxazolyl, triazolyl, tetrazolyl, thiadiazolyl, pyridinyl, pyrimidinyl, pyridazinyl, pyrazinyl, benzofuranyl, benzothienyl, benzothiadiazolyl, benzothiazolyl, benzimidazolyl, indolyl, isoindolyl, indazolyl, quinolyl, isoquinolyl, quinazolinyl, 1,2,3,4-tetrahydroisoquinolyl, [pyrro] *pyrrolo*[2,3-c]pyridinyl, [pyrro] *pyrrolo*[3,2-c]pyridinyl, [pyrro] *pyrrolo*[2,3-b]pyridinyl, [pyrro] *pyrrolo*[3,2-b]pyridinyl, [pyrro] *pyrrolo*[2,3b] pyrazinyl, indolin-2-onyl, preferably indolyl, indazolyl, [pyrro] *pyrrolo*[2,3-c]pyridinyl, [pyrro] *pyrrolo*[3,2-c] pyridinyl, [pyrro] *pyrrolo*[2,3-b]pyridinyl, [pyrro] *pyrrolo* [3,2-b]pyridinyl, [pyrro] *pyrrolo*[2,3-b]pyrazinyl, indolin-2-onyl, pyridinyl, pyrazolyl or pyrimidinyl, imidazolyl, pyrazinyl, benzimidazolyl, indolyl, isoindolyl or 1,2,3,4-tetrahydroisoquinolyl, more preferably indolyl, indazolyl, [pyrro] *pyrrolo*[2,3-c]pyridinyl, [pyrro] *pyrrolo*[3,2-c] pyridinyl, [pyrro] *pyrrolo*[2,3-b]pyridinyl, [pyrro] *pyrrolo* [3,2-b]pyridinyl, [pyrro] *pyrrolo*[2,3-b]pyrazinyl, indolin-2-onyl, pyridinyl, pyrazolyl or pyrimidinyl.

The present invention also includes the pharmaceutically acceptable salt of the compound represented by formula (I). The term "pharmaceutically acceptable salt" means relatively nontoxic acid addition salts or base addition salts of the compound of the present invention. Said acid addition salts are the salts formed between the compound represented by formula (I) of the present invention and suitable inorganic acids or organic acids. Said salts may be prepared during the final separation and purification processes of the compounds, or may be prepared through the reaction of purified compound represented by formula (I) in the form of free base thereof and suitable organic acids or inorganic acids. Representative acid addition salts includes hydrobromic acid salt, hydrochloric acid salt, sulfate, bisulfate, sulfite, acetate, oxalate, valerate, oleate, palmate, stearate, laurate, borate, benzoate, lactate, phosphate, hydrogen phosphate, carbonate, bicarbonate, toluate, citrate, maleate, fumarate, succinate, tartrate, benzoate, mesylate, p-tosylate, glyconate, lactobionate and laurylsulfonate and the like. Said base addition salts are the salts formed between the compound represented by formula (I) and suitable inorganic bases or organic bases, including such as the salts formed with alkali metals, alkaline earth metals, quaternary ammonium cations, such as sodium salts, lithium salts, potassium salts, calcium salts, magnesium salts, tetramethylammonium salts, tetraethylammonium salt and the like; amine salts, including the salts formed with ammonia ($NH_3$), primary amines, secondary amines or tertiary amines, such as: methylamine salts, dimethylamine salts, trimethylamine salts, triethylamine salts, ethylamine salts and the like.

The compound of the present invention or a pharmaceutically acceptable salt thereof can be administered to mammals, such as human, and administrated orally, rectally, parenterally (intravenously, intramuscularly or subcutaneously), topically (such as in the form of powders, ointments or drops), or intratumorally.

The administration dosage of the compound of the present invention can be about 0.05-50 mg/kg body weight/day, e.g. 0.1-45 mg/kg body weight/day, 0.5-35 mg/kg body weight/day.

The compound of the present invention or a pharmaceutically acceptable salt thereof can be formulated into the solid dosage fonns for oral administration, which includes but is not limited to capsules, tablets, pills, powders and granules and the like. In these solid dosage forms, the compounds represented by formula (I) of the present invention as active ingredients are admixed with at least one conventional inert excipients (or carriers), such as sodium citrate or dicalcium phosphate, or admixed with the following ingredients: (1) fillers or extenders, such as, starch, lactose, sucrose, glucose, mannitol and silicic acid and the like; (2) adhesives, such as, hydroxymethylcellulose, alginate, gelatin, polyvinyl pyrrolidine, sucrose and acacia and the like; (3) humectants, such as, glycerol and the like; (4) disintegrating agents, such as, agar, calcium carbonate, potato starch or tapioca, alginic acid, certain composite silicate and sodium carbonate and the like; (5) retarding solvents, such as paraffin wax and the like; (6) absorption accelerators, such as, quaternary ammonium compounds and the like; (7) moistening agents, such as cetanol and glyceryl monostearate and the like; (8) absorbents, such as, kaolin and the like; and (9) lubricants, such as, talc, calcium stearate, magnesium stearate, solid polyethylene glycol, sodium dodecyl sulphate and the like, or mixtures thereof. Capsules, tablets and pills may also comprise buffers.

Said solid dosage forms such as tablets, sugar pills, capsules, pills and granules can also by coated or microencapsulated by coatings and shell materials such as enteric coatings and other materials well known in the art. They may comprise opacifying agents, and the release of active ingredients in these compositions may be carried out in a certain portion of digestive tube in a retarded manner. The examples for embedding components that may be adopted are polymers and waxes. If necessary, active ingredients can also be formulated into the form of microcapsules with one or more of the above excipients.

The compound of the present invention or a pharmaceutically acceptable salt thereof can be formulated into liquid dosage forms for oral administration, including but not limited to pharmaceutically acceptable emulsions, solutions, suspensions, syrups and tinctures and the like. Besides the compounds represented by formula (I) or a pharmaceutically acceptable salt thereof as active ingredients, the liquid dosage forms may comprise inert diluents customarily used in the art, such as water and other solvents, solubilizers and emulsifiers, such as, ethanol, isopropyl alcohol, ethyl carbonate, ethyl acetate, propylene glycol, 1,3-butanediol, dimethyl formamide, and oils, especially cottonseed oil, peanut oil, corn germ oil, olive oil, castor oil and sesame oil and the like or mixtures of these materials and the like. Besides these inert diluents, the liquid dosage forms of the present invention may also comprise conventional auxiliaries, such as moistening agents, emulsifiers and suspending agents, sweeting agents, flavoring agents and fragrances and the like.

Said suspending agents includes, such as, ethoxylated isostearyl alcohol, polyoxyethylene sorbitol and sorbitan ester, microcrystalline cellulose, aluminium methoxide and agar and the like or mixtures of these materials.

The compound of the present invention or a pharmaceutically acceptable salt thereof can be formulated into dosage forms for parenteral injection, including but not limited to physiologically acceptable sterile aqueous or anhydrous solutions, dispersions, suspensions or emulsions, and sterile powder for re-dissolving into sterile injectable solutions or dispersions. Suitable carriers, diluents, solvents or excipients include water, ethanol, polyhydric alcohol and suitable mixtures thereof.

The compound of the present invention or a pharmaceutically acceptable salt thereof can also be formulated into dosage forms for topical administration, including but not limited to ointments, powders, suppositories, drops, propellants and inhalants and the like. The compounds represented by formula (I) of the present invention or a pharmaceutically acceptable salt thereof as active ingredients are admixed together with physiologically acceptable carriers and optional preservatives, buffers, or if necessary, propellants, under sterile condition.

The present invention also provides a pharmaceutical composition containing the compound represented by formula (I) of the present invention or a pharmaceutically acceptable salt thereof as active ingredients, and pharmaceutically acceptable carriers, excipients or diluents. When preparing the pharmaceutical composition, the compound represented by formula (I) of the present invention or a pharmaceutically acceptable salt thereof is generally admixed with pharmaceutically acceptable carriers, excipients or diluents. The content of the compound of the general formula (I) or a pharmaceutically acceptable salt thereof can be 0.01-1000 mg, for example 0.05-800 mg, 0.1-500 mg, 0.01-300 mg, 0.01-200 mg, 0.05-150 mg, 0.05-50 mg and the like.

By conventional preparation methods, the composition of the present invention may be formulated into conventional pharmaceutical preparations, such as tablets, pills, capsules, powder, granules, emulsions, suspensions, dispersions, solutions, syrups, elixirs, ointments, drops, suppositories, inhalants, propellants and the like.

The compound of the present invention or a pharmaceutically acceptable salt thereof may be administered alone or in combination with other pharmaceutically acceptable therapeutic agents, especially with other anti-tumor drugs. The therapeutic agents include but are not limited to anti-tumor drugs which exert an influence on the chemical structure of DNA, such as Cisplatin, anti-tumor drugs which affect the synthesis of nucleic acid, such as Methotrexate (MTX), 5-Fluorouracil (5FU) and the like, anti-tumor drugs which affect the transcription of nucleic acid, such as Adriamycin, Epirubicin, Aclacinomycin, Mitramycin and the like, anti-tumor drugs which exert an influence on synthesis of tubulin, such as Paclitaxel, Vinorelbine and the like, aromatase inhibitors such as Aminoglutethimide, Lentaron, Letrozole, Anastrozole and the like, inhibitors of the cell signal pathway such as epidermal growth factor receptor inhibitors Imatinib, Gefitinib, Erlotinib, and the like. Each therapeutic agent to be combined can be administered simultaneously or sequentially, and can be administered either in a unitary formulation or in separate formulations. Such combination includes not only the combination of the compound of the present invention with another active ingredient but also the combination of the compound of the present invention with two or more other active ingredients.

It is proved by the cell experiments, i.e., in vitro proliferation inhibition experiments on the activating mutation, i.e., Exon 19 deletion activating mutation tumor cells, such as HCC827 cell, resistant tumor cells such as H1975 and thewild-type EGFR human skin cancer cell A431 that, the compound of the present invention has a good proliferation inhibition effect on the activating mutation or resistant mutation tumor cells and a weak proliferation inhibition effect on the wild-type EGFR cancer cells, and has a good selectivity. It is proved by the animal experiment, i.e., the experiment of inhibiting the growth of subcutaneously transplanted tumors of human lung cancer H1975-bearing nude mice that, the compound of the present invention has a good inhibition effect on the growth of the transplanted tumor and a good safety. The compound of the present invention can be used as the medicament for treating a disease or condition mediated by the activity of EGFR activating or resistant mutation, in particular tumor, e.g. cancer. Said cancer includes but is not limited to, e.g. lung cancer, ovarian cancer, cervical cancer, breast cancer, stomach cancer, colorectal cancer, pancreatic cancer, glioma, glioblastoma, melanoma, prostate cancer, leukemia, lymphoma, nonHodgkin's lymphoma, hepatocytes cancer, gastrointestinal stromal tumor (GIST), thyroid cancer, cholangiocarcinoma, endometrial cancer, renal cancer, anaplastic large cell lymphoma, acute myeloid leukemia (AML), multiple myeloma, mesothelioma, in particular a type of tumor wherein threonine at position 790 of the epidermal growth factor receptor is mutated into methionine (EGFR T790M). For example, the compound of the present invention can be used as medicament for treating the non-small cell cancer (EGFR T790M). It can be used to overcome the resistency problem caused by EGFR T790M after Gefitinib and Erlotinib are clinically used. Due to the reduced toxicity associated with the inhibition of the wild-type EGFR, it is therefore expected that the compound of the present invention will produce a relatively small toxic and side-effect upon being applied to the cancer treatment.

The pharmacodynamic action of the compound of the present invention in terms of inhibiting the proliferation of cancer cells may be assayed by conventional methods. One preferable evaluation method of which is Sulforhodamine B (SRB) protein staining method, which calculates the inhibition ratio of a drug against the proliferation of cancer cells by measuring the change in optical absorption value generated after the drug has acted on the cancer cells.

$$\text{Inhibition ratio (\%)}=[(\text{blank control OD}-\text{inhibitor OD})/\text{blank control OD}]\times 100\%$$

Blank control OD: the OD value of the well of normally growed cells without the action of a drug.

Inhibitor OD: the OD value of the well of cells with the action of the added compounds to be screened.

The median inhibitory concentration ($IC_{50}$) value is obtained by the software GraphPad Prism 5.0 by the 4-parameter logistic curve fit calculation. Each experiment is repeated three times, and the average $IC_{50}$ value for three experiments is used as the final index for the inhibitory ability.

The pharmacodynamic action of the compound of the present invention in terms of inhibiting the growth of transplanted tumors in animal may be assayed by conventional methods. One preferable evaluation method of which is the inhibitory effect on the growth of subcutaneously transplanted tumors of human lung cancer H1975-bearing nude mice. The experimental method is as follows: human lung cancer H1975 cell strain ($5\times10^6$/each mouse) is inoculated to nude mice subcutaneously at the right side of the back thereof. After the tumors grow to 100-150 $mm^3$ on average, the animals are divided into groups randomly according to the tumor size and the animal weight. The test compounds are administered by intragastric administration in a certain dosages, and solvent control groups are administered with equal amount of solvent by intragastric administration, wherein the administration is performed once per day for a continuous period of 12 days. During the entire experimental process, the animal weight and the tumor size are measured twice per week, so as to observe whether or not the toxic reaction occurs. The tumor volume is calculated as follows:

$$\text{Tumor volume } (mm^3)=0.5\times(\text{Tumor major diameter}\times\text{Tumor minor diameter}^2)$$

Figure 1:
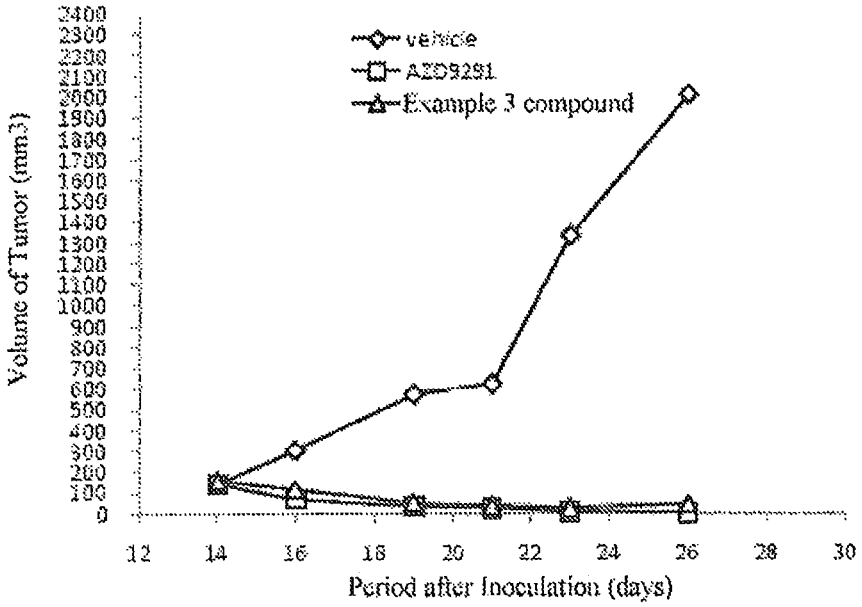
FIG. 1 is the tumor volume curve for subcutaneously transplanted tumors of human lung cancer H1975-bearing nude mice at the administration dosage of 25 mg/kg of the compound of Example 3 and AZD9291.

The present invention will be further illustrated hereinafter in connection with specific Examples. It should be understood that these Examples are only used to illustrate the present invention by the way of examples without limiting the scope thereof. In the following Examples, the experimental methods without specifying conditions are generally performed according to conventional conditions or based on the conditions recommended by the manufacturer. The parts and percentages are the parts and percentages by weight respectively, unless otherwise specified.

DETAILED DESCRIPTION OF THE INVENTION

1. Preparation Examples of the Compounds of the Present Invention

Intermediate 1a: $N^2$-methyl-$N^2$-[2-(dimethylamino) ethyl]-6-methoxy-3-nitropyridin-2,5-diamine hydrochloride (Intermediate 1a)

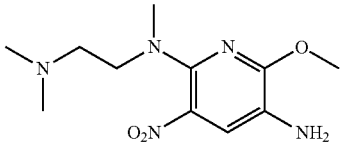

Step 1: Synthesis of 6-chloro-2-methoxy-3-nitropyridine

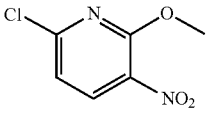

To a 250 mL three-necked flask were added 2,6-dichloro-3-nitropyridine (11.58 g, 60 mmol), 150 ml tetrahydrofuranand methanol (1.92 g, 60 mmol). The mixture was cooled to 0° C. To the mixture was added in batch 60% sodium hydride (2.4 g, 60 mmol). The resulting mixture was stirred at 0° C. for 1 hour, warmed up slowly to room temperature, and continued to stir for 1 hour. To the reaction mixture was added 100 ml ethyl acetate. The reaction mixture was washed successively with water (50 ml×2) and saturated brine (50 ml). The organic phase was dried with anhydrous sodium sulfate, filtered, evaporated under a reduced pressure to remove the solvent, purified by silica gel column chromatography (petroleum ether:ethyl acetate=30:1) to produce 7.3 g of a product with a yield of 64%.

$^1$H NMR (400 MHz, $CDCl_3$) δ 8.29 (d, J=8.3 Hz, 1H), 7.07 (d, J=8.3 Hz, 1H), 4.15 (s, 3H).

Step 2: Synthesis of 6-chloro-2-methoxypyridin-3-amine

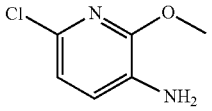

To a 100 mL single-necked flask were added 6-chloro-2-methoxy-3-nitropyridine (2.0 g, 10.6 mmol), ammonia chloride (2.8 g, 53.0 mmol) and 80 ml of a mixed solvent of ethanol and water (volume ratio=3:1). To the mixture was added in batch a reduced iron powders (3.0 g, 53.0 mmol). The mixture was stirred at 80° C. for 1.5 hours. The reaction mixture was cooled to room temperature, and filtered through diatomite. 150 ml ethyl acetate and 120 ml saturated sodium chloride were added to the filtrate. An organic layer was separated and dried with anhydrous sodium sulfate, and filtered. The filtrate was evaporated to dryness under a reduced pressure to produce a brown solid (1.6 g) with a yield of 95%. MS m/z: 159 [M+1].

Step 3: Synthesis of N-(6-chloro-2-methoxypyridin-3-yl)acetamide

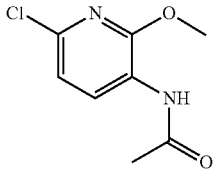

To a 250 mL single-necked flask were added 6-chloro-2-methoxypyridin-3-amine (1.6 g, 10.1 mmol), diisopropylethylamine (2.6 ml, 15.1 mmol) and 100 ml dichloromethane. The mixture was cooled to 5° C. in an ice bath. Acetyl chloride (0.86 ml, 12.1 mmol) was added. The reaction continued for 1.25 hours. The reaction mixture was washed successively with 80 ml water, 80 ml 1N hydrochloric acid and 80 ml saturated sodium chloride solution, dried with anhydrous sodium sulfate, filtered, and evaporated to dryness under a reduced pressure to produce 1.9 g of a brown solid with a yield of 94%. MS m/z: 201 [M+1].

Step 4: Synthesis of N-(6-chloro-2-methoxy-5-nitropyridin-3-yl)acetamide

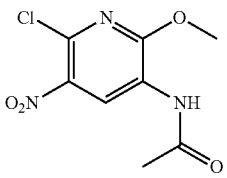

To a 100 mL single-necked flask were added N-(6-chloro-2-methoxypyridin-3-yl)acetamide (1.9 g, 9.47 mmol) and 20 ml trifluoroacetic anhydride. The mixture was cooled in an ice-salt bath to −10° C. Fuming nitric acid (0.4 ml, 9.47 mmol) was dropwisely added while the temperature was controlled to below −5° C. After the completion of dropwise addition, the reaction continued in an ice-salt bath for 1.25 hours. The reaction mixture was slowly added to crushed ice. A solid precipitated and was filtered. The resulting crude product was dried at 60° C., and added to ethyl acetate to form a slurry. 1.5 g of an beige solid was obtained with a yield of 65%. MS m/z: 244 [M−1].

$^1$H NMR (400 MHz, DMSO-d6) δ 9.90 (s, 1H), 9.17 (s, 1H), 4.06 (s, 3H), 2.17 (s, 3H).

Step 5: Synthesis of N-{6-{[2-(dimethylamino)ethyl](methyl)amino}-2-methoxy-5-nitropyridin-3-yl}acetamide hydrochloride

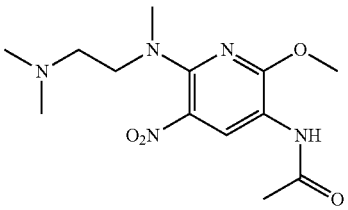

To a 100 mL single-necked flask were added N-(6-chloro-2-methoxy-5-nitropyridin-3-yl)acetamide (1.0 g, 4.1 mmol), 30 ml acetonitrile and N,N,N'-trimethylethylenediamine (0.6 g, 6.1 mmol). The mixture was reacted at 80° C. for 3 hours. The reaction mixture was concentrated under a reduced pressure to about ⅓ of the original volume. 50 ml ethyl acetate was added. The mixture was stirred for several minutes, a solid precipitated and was filtered to produce 1.1 g of an beige solid with a yield of 87%.

$^1$H NMR (400 MHz, DMSO-d6) δ 11.13 (s, 1H), 9.53 (s, 1H), 8.73 (s, 1H), 4.05 (s, 5H), 3.41 3.36 (m, 2H), 2.83 (s, 3H), 2.80 (s, 6H), 2.07 (s, 3H).

Step 6: Synthesis of $N^2$-methyl-$N^2$-[2-(dimethylamino)ethyl]-6-methoxy-3-nitropyridin-2,5-diamine hydrochloride (Intermediate 1a)

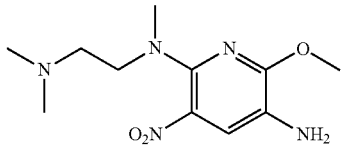

To a 50 mL single-necked flask were added N-{6-{[2-(dimethylamino)ethyl](methyl)amino}-2-methoxy-5-nitropyridin-3-yl}acetamide (600 mg, 1.93 mmol), 15 ml methanol and 0.3 ml concentrated hydrochloric acid. The mixture was reacted at 60° C. overnight. The reaction mixture was evaporated to dryness under a reduced pressure. 100 ml dichloromethane and 80 ml saturated sodium bicarbonate were added. The resulting mixture was stirred until no bubble produced. An organic layer was separated and dried with anhydrous sodium sulfate, filtered, and concentrated under a reduced pressure. The residue was purified by silica gel column chromatography (dichloromelhanemethanol=10:1) to produce 400 mg of a brown solid. MS m/z: 270 [M+1].

$^1$H NMR (400 MHz, DMSO-d6) δ 11.20 (s, 1H), 8.16 (s, 1H), 4.06-4.02 (m, 5H), 3.38 (br s, 2H), 2.83 (s, 3H), 2.80 (s, 3H), 2.79 (s, 3H).

Intermediate 1b: Synthesis of $N^2$-methyl-$N^2$-[2-(dimethylamino)ethyl]-6-isopropyloxy-3-nitropyridin-2,5-diamine (Intermediate 1b)

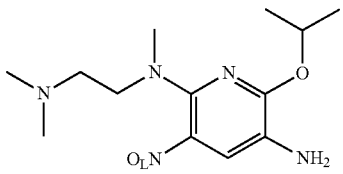

Step 1: Synthesis of 6-chloro-2-isopropyloxy-3-nitropyridine

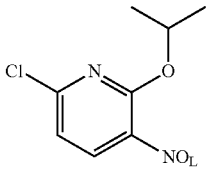

The compound was synthesized in the same manner as those in Step 1 of Intermediate 1a.

$^1$H NMR (400 MHz, $CDCl_3$) δ 8.22 (d, J=8.3 Hz, 1H), 6.98 (d, J=8.3 Hz, 1H), 5.50 (kept, J=6.2 Hz, 1H), 1.43 (d, J=6.2 Hz, 6H).

Step 2: Synthesis of 6-chloro-2-isopropyloxypyridin-3-amine

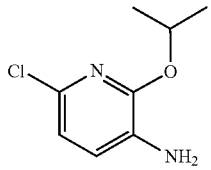

The compound was synthesized in the same manner as those in Step 2 of Intermediate 1a with a yield of 74%. MS m/z: 187 [M+1], 189.

Step 3: Synthesis of N-(6-chloro-2-isopropyloxypyridin-3-yl)acetamide

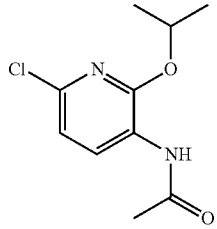

The compound was synthesized in the same manner as those in Step 3 of Intermediate 1a with a yield of 83%. MS m/z: 229 [M+1], 231.

Step 4: Synthesis of N-(6-chloro-2-isopropyloxy-5-nitropyridin-3-yl)acetamide

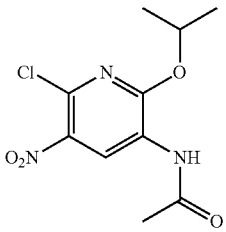

The compound was synthesized in the same manner as those in Step 4 of Intermediate 1a with a yield of 33%. MS m/z: 272 [M−1].

Step 5: Synthesis of N-{6-{[2-(dimethylamino) ethyl](methyl)amino}-2-isopropyloxy-5-nitropyridin-3-yl}acetamide

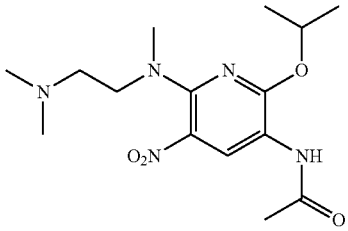

To a 500 mL single-necked flask were added N-(6-chloro-2-isopropyloxy-5-nitropyridin-3-yl)acetamide (15 g, 54.8 mmol), 150 ml acetonitrile, N,N,N'-trimethylethylenediamine (7.28 g, 71.3 mmol) and potassium carbonate (15.15 g, 110 mmol). The mixture was reacted at 80° C. overnight. The reaction mixture was cooled to room temperature, and filtered. The filtrate was evaporated to dryness under a reduced pressure to produce 18.6 g of a product with a yield of 100%.

MS m/z: 340 [M+1].

Step 6: Synthesis of $N^2$-methyl-$N^2$-[2-(dimethylamino)ethyl]-6-isopropyloxy-3-nitropyridin-2,5-diamine (Intermediate 1b)

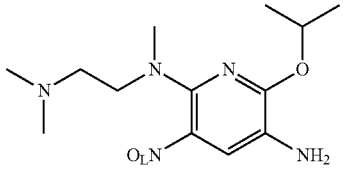

The compound was synthesized in the same manner as those in Step 6 of Intermediate 1a with a yield of 38%. MS m/z: 298 [M+1].

Intermediate 1c: $N^2$-methyl-$N^2$-[2-(dimethylamino) ethyl]-6-(2,2,2-trifluoroethoxyl)-3-nitropyridin-2,5-diamine (Intermediate 1c)

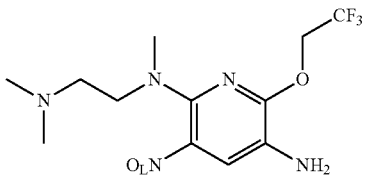

Step 1: Synthesis of 6-chloro-2-(2,2,2-trifluoroethoxyl)-3-nitropyridine

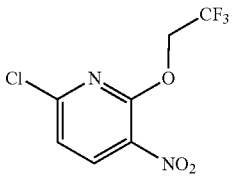

The compound was synthesized in the same manner as those in Step 1 of Intermediate 1a with a yield of 80%.

Step 2: Synthesis of 6-chloro-2-(2,2,2-trifluoroethoxyl)pyridin-3-amine

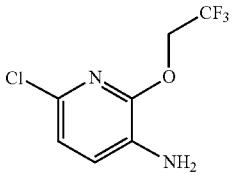

The compound was synthesized in the same manner as those in Step 2 of Intermediate 1a with a yield of 83%.

Step 3: Synthesis of N-[6-chloro-2-(2,2,2-trifluoroethoxyl)pyridin-3-yl]acetamide

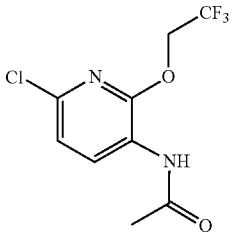

The compound was synthesized in the same manner as those in Step 3 of Intermediate 1a with a yield of 71%. MS m/z: 269 [M+1], 271.

Step 4: Synthesis of N-[6-chloro-2-(2,2,2-trifluoroethoxyl)-5-nitropyridin-3-yl]acetamide

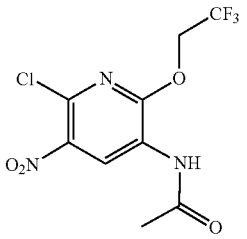

The compound was synthesized in the same manner as those in Step 4 of Intermediate 1a with a yield of 53%. MS m/z: 314 [M+1], 316.

$^1$H NMR (400 MHz, $CDCl_3$) δ 9.37 (s, 1H), 7.63 (s, 1H), 4.93 (q, J=8.2 Hz, 2H), 2.30 (s, 3H).

Step 5: Synthesis of N-{6-{[2-(dimethylamino)ethyl](methyl)amino}-2-(2,2,2-trifluoroethoxyl)-5-nitropyridin-3-yl}acetamide

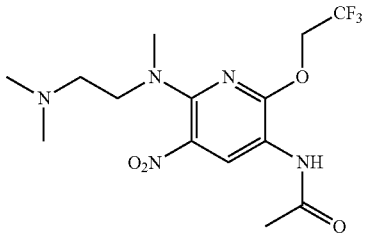

To a 25 mL single-necked flask were added N-[6-chloro-2-(2,2,2-trifluoroethoxyl)]-5-nitropyridin-3-ypacetamide (626 mg, 2 mmol), 10 ml acetonitrile, N,N,N'-trimethylethylenediamine (224 mg, 2.2 mmol) and potassium carbonate (138 mg, 4 mmol). The mixture was stirred at room temperature overnight. To the reaction mixture was added 100 ml ethyl acetate. The resulting mixture was washed with 20 ml water, dried with anhydrous sodium sulfate, and evaporated under a reduced pressure to remove the solvent to produce 710 mg of a product with a yield of 94%. MS m/z: 380 [M+1].

Step 6: Synthesis of $N^2$-methyl-$N^2$-[2-(dimethylamino)ethyl]-6-(2,2,2-trifluoroethoxyl)-3-nitropyridin-2,5-diamine (Intermediate 1c)

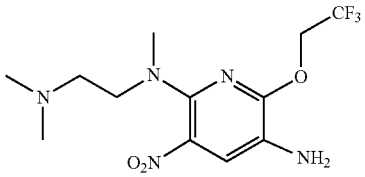

The compound was synthesized in the same manner as those in Step 6 of Intermediate 1a with a yield of 100%. MS m/z: 338 [M+1].

Intermediate 1d: tert-butyl {5-acrylamide-6-{[2-(dimethylamino)ethyl](methyl)amino}-2-isopropyloxypyridin-3-yl}carbamate (Intermediate 1d)

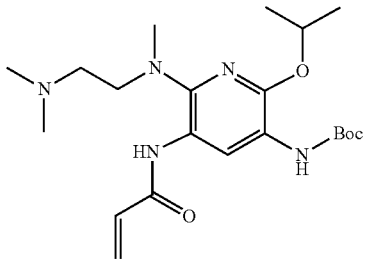

Step 1: Synthesis of N-tert-butoxycarbonyl-N-{6-{[2-(dimethylamino)ethyl](methyl)amino}-2-isopropyloxy-5-nitropyridin-3-yl}acetamide

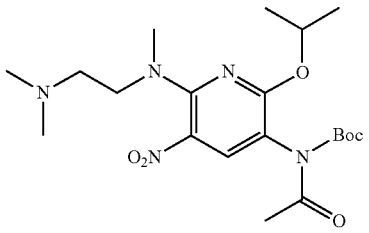

To a 500 mL single-necked flask were added N-{6-{[2-(dimethylamino)ethyl](methyl)amino}-2-isopropyloxy-5-nitropyridin-3-yl}acetamide (18.6 g, 54.8 mmol), 4-dimethylaminopyridine (0.67 g, 5.48 mmol), 150 ml acetonitrile and di-tert-butyl dicarbonate (59.8 g, 274 mmol). The mixture was reacted at 80° C. for 2.5 hours. The reaction mixture was cooled to room temperature, was evaporated to dryness under a reduced pressure, and purified by silica gel column chromatography (dichloromethane methanol=10:1) to produce 24 g of a product with a yield of 100%.

Step 2: Synthesis of tert-butyl {6-({[2-(dimethylamino)ethyl](methyl)amino}-2-isopropyloxy-5-nitropyridin-3-yl}carbamate

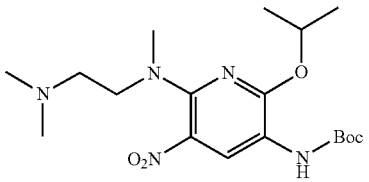

To a 500 mL single-necked flask were added N-tertbutoxycarbonyl-N-{6-{[2-(dimethylamino)ethyl](methyl)amino}-2-isopropyloxy-5-nitropyridin-3-yl}acetamide (24 g, 54.6 mmol) and 240 ml methanol. The mixture was cooled to 0° C. Sodium methoxide (2.95 g, 54.6 nunol) was added. The mixture was slowly warmed up to room temperature and reacted overnight. The reaction mixture was concentrated under a reduced pressure. The residue was dissolved in 300 ml ethyl acetate, and washed with 100 ml water. The organic phase was dried with anhydrous sodium sulfate, filtered, and evaporated to dryness under a reduced pressure to produce 18 g of a product with a yield of 83%.

Step 3: Synthesis of tert-butyl {5-amino-6-{[2-(dimethylamino)ethyl](methyl)amino}-2-isopropyloxypyridin-3-yl}carbamate

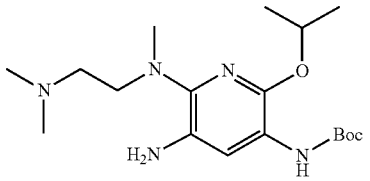

The compound was synthesized in the same manner as those in Step 2 of Intermediate 1a with a yield of 97%.

MS m/z: 368 [M+1].

$^1$H NMR (400 MHz, DMSO-d6) δ 7.61 (s, 1H), 7.44 (s, 1H), 6.74 (br s, 2H), 5.09-4.96 (m, 1H), 3.29 (t, J=5.8 Hz, 2H), 3.19 (t, J=5.7 Hz, 2H), 2.70 (s, 6H), 2.56 (s, 3H), 1.45 (s, 9H), 1.26 (d, J=6.2 Hz, 6H).

Step 4: Synthesis of tert-butyl {5-acrylamide-6-{[2-(dimethylamino)ethyl](methyl)amino}-2-isopropyloxypyridin-3-yl}-carbamate (Intermediate 1d)

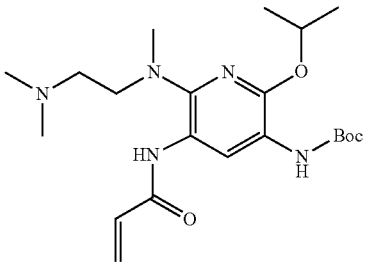

To a 500 ml three-necked flask were added tert-butyl {5-amino-6-{[2-(dimethylamino)ethyl](methyl)amino}-2-isopropyloxypyridin-3-yl}carbamate (9 g, 24.49 mmol), trimethylamine (6.83 ml, 49.0 mmol) and 250 ml dichloromethane. The reaction mixture was cooled in an ice-water bath to below 5° C. Acryloyl chloride (2.1 ml, 25.7 mmol) was dropwisely added. The resulting mixture was continued to react for 1 hour. The reaction mixture was washed successively with 150 ml saturated sodium bicarbonate solution and 150 ml saturated brine, dried with anhydrous sodium sulfate, and filtered. The filtrate was evaporated to dryness under a reduced pressure to produce 5 g of a product with a yield of 48%. MS m/z: 422 [M+1].

$^1$H NMR (400 MHz, DMSO-d6) δ 9.76 (s, 1H), 8.16 (s, 1H), 7.88 (s, 1H), 6.44 (dd, J=17.0, 10.1 Hz, 1H), 6.22 (dd, J=17.0, 1.9 Hz, IH), 5.74 (dd, J=10.1, 1.9 Hz, 1H), 5.22-5.13 (m, 1H), 3.09 (t, J=6.5 Hz, 2H), 2.77 (s, 3H), 2.41 (t, J=6.5 Hz, 2H), 2.18 (s, 6H), 1.45 (s, 9H), 1.31 (d, J=6.2 Hz, 6H).

Intermediate 1e: tert-butyl {5-acrylamide-6-{[2-(dimethylamino)ethyl](methyl)amino}-2-(2,2,2-trifluoroethoxyl)pyridin-3-yl}carbamate (Intermediate 1e)

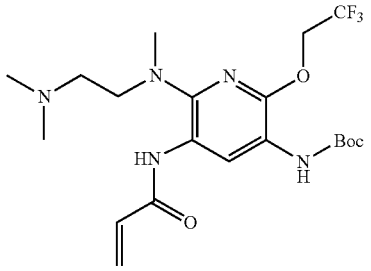

The compound was synthesized in the same manner as those in Step 1 of Intermediate 1d with a yield of 99%. MS m/z: 480 [M+1].

Step 2: Synthesis of tert-butyl {6- f[2-(dimethylamino)ethyl](methypamino}-2-(2,2,2-trifluoroethoxyl)-5-nitropyridin-3-ylIcarbamate

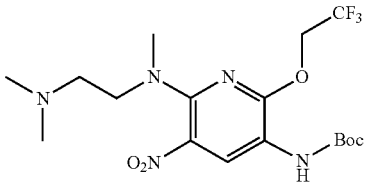

The compound was synthesized in the same manner as those in Step 2 of Intermediate 1d with a yield of 88%. MS m/z: 438 [M+1].

Step 3: Synthesis of tert-butyl {5-amino-6-{[2-(dimethylamino)ethyl](methyl)amino}-2-(2,2,2-trifluoroethoxyl)pyridin-3-yl}carbamate

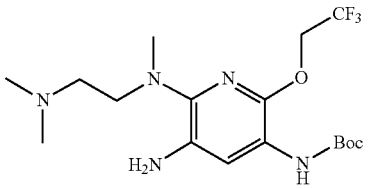

The compound was synthesized in the same manner as those in Step 2 of Intermediate 1a with a yield of 76%. MS m/z: 408 [M+1].

Step 4: Synthesis of tert-butyl {5-acrylamide-6-{[2-(dimethylamino)ethyl](methyl0amino}-2-(2,2,2-trifluoroethoxyl)pyridin-3-yl}carbamate (Intermediate 1e)

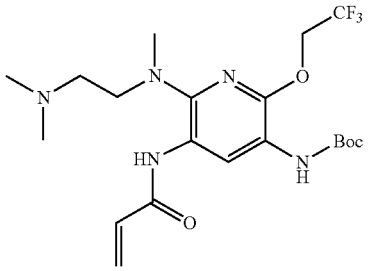

The compound was synthesized in the same manner as those in Step 4 of Intermediate 1d with a yield of 62%. MS m/z: 462 [M+1].

$^1$H NMR (400 MHz, $CDCl_3$) δ 10.11 (s, 1H), 9.35 (s, 1H), 6.61 (s, 1H), 6.46 (dd, J=16.9, 1.7 Hz, 1H), 6.39-6.25 (m, 1H), 5.70 (dd, J=10.0, 1.8 Hz, 1H), 4.76 (q, J=8.5 Hz, 2H), 2.96 (s, 2H), 2.71 (s, 3H), 2.42 (s, 2H), 2.34 (s, 6H), 1.53 (s, 9H).

Intermediate 2a: 3-(2-chloropyrimidin-4-yl)-1-methyl-1H-indole (Intermediate 2a)

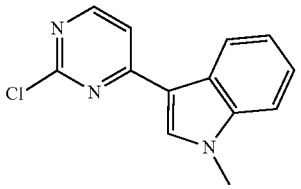

To a 500 mL single-necked flask were added 2,4-dichloropyrimidine (14.9 g, 100 mmol), 1-methyl-1H-indole (13 g, 100 mmol), 200 ml 1,2-diclaloroethane and aluminium chloride (13.9 g, 120 mmol). The mixture was stirred at 80° C. for 1.5 hours. The reaction mixture was cooled to room temperature in an ice bath. 120 ml methanol and 400 ml water were added to quench the reaction. A solid precipitated and was filtered. The filter cake was washed with methanol, and dried in vacuum to produce 17.2 g of a product with a yield of 71%. MS m/z: 244 [M+1], 246.

$^1$H NMR (400 MHz, DMSO-d6) δ 8.53 (d, J=5.5 Hz, 1H), 8.49 (s, 1H), 8.42 (dd, J=7.0, 1.5 Hz, 1H), 7.81 (d, J=5.5 Hz, 1H), 7.56 (dd, J=7.0, 1.2 Hz, 1H), 7.33-7.26 (m, 2H), 3.90 (d, J=5.2 Hz, 3-H).

Intermediate 2b: 3-(2,5-dichloropyrimidin-4-yl)-1-methyl-1H-indole (Intermediate 2b)

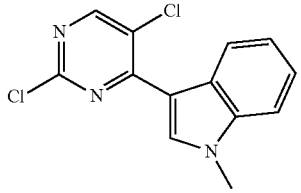

The compound was synthesized in the same manner as those in Intermediate 2a with a yield of 87%. MS m/z: 278[M+1], 279, 280.

$^1$H NMR (400 MHz, DMSO-d6) δ 8.79 (s, 1H), 8.74 (s, 1H), 8.56 (dd, J=7.3, 1.2 Hz, 1H), 7.62 (d, J=7.6 Hz, 1H), 7.39-7.34 (m, 1H), 7.34-7.29 (m, 1H), 3.97 (s, 3H).

Intermediate 2c: 3-(2-chloropyrimidin-4-yl)-1-methyl-5-fluoro-1H-indole (Intermediate 2c)

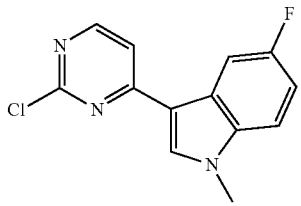

The compound was synthesized in the same manner as those in Intermediate 2a with a yield of 29%. MS m/z: 262 [M+1], 264.

$^1$H NMR (400 MHz, DMSO-d6) δ 8.55 (s, 1H), 8.53 (d, J=5.5 Hz, 1H), 8.10 (dd, J=10.3, 2.5 Hz, 1H), 7.80 (d, J=5.5 Hz, 1H), 7.60 (dd, J=8.9, 4.6 Hz, 1H), 7.17 (td, J=9.1, 2.6 Hz, 1H), 3.90 (s, 3H).

Intermediate 2d: 3-(2-chloropyrimidin-4-yl)-1-methyl-6-fluoro-1H-indole (Intermediate 2d)

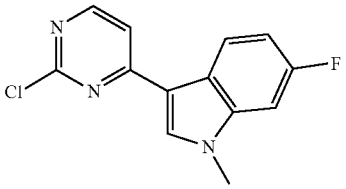

The compound was synthesized in the same manner as those in Intermediate 2a. MS m/z: 262 [M+1], 264.

$^1$H NMR (400 MHz, DMSO-d6) δ 8.54 (d, J=5.5 Hz, 1H), 8.49 (s, 1H), 8.39 (dd, J=8.8, 5.6 Hz, 1H), 7.81 (d, J=5.5 Hz, 1H), 7.47 (dd, J=9.9, 2.3 Hz, 1H), 7.14 (td, J=9.6, 2.4 Hz, 1H), 3.86 (s, 3H).

Intermediate 2e: 3-(2-chloropyrimidin-4-yl)-1-methyl-5,6-difluoro-1H-indole (intermediate 2e)

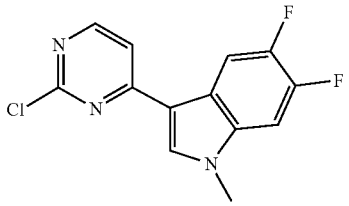

The compound was synthesized in the same manner as those in Intermediate 2a. MS m/z: 280 [M+1], 282.

$^1$H NMR (400 MHz, DMSO-d6) δ 8.54 (d, J=5.5 Hz, 1H), 8.52 (s, 1H), 8.22 (dd, J=11.7, 8.2 Hz, 1H), 7.79 (d, J=5.5 Hz, 1H), 7.73 (dd, J=11.2, 7.0 Hz, 1H), 3.86 (s, 3H).

Intermediate 2f: 3-(2,5-dichloropyrimidin-4-yl)-1-methyl-6-fluoro-1H-indole (Intermediate 2f)

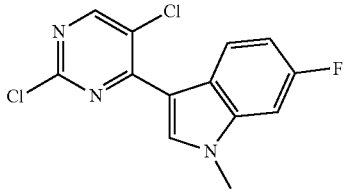

The compound was synthesized in the same manner as those in Intermediate 2a. MS m/z: 296 [M+1], 297, 298.

$^1$H NMR (400 MHz, $CDCl_3$) δ 8.69 (dd, J=8.9, 5.5 Hz, 1H), 8.50 (s, 1H), 8.41 (s, 1H), 7.17 7.07 (m, 2H), 3.90 (s, 3H).

Intermediate 2g: 3-(2,5-dichloropyrimidin-4-yl)-1-methyl-5,6-difluoro-1H-indole (Intermediate 2g)

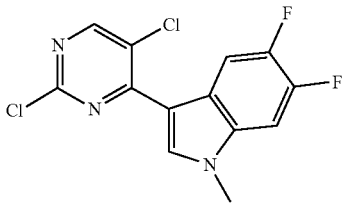

The compound was synthesized in the same manner as those in Intermediate 2a. MS m/z: 314 [M+1], 315, 316.

$^1$H NMR (400 MHz, DMSO-d6) δ 8.85 (s, 1H), 8.77 (s, 1H), 8.39 (dd, J=12.1, 8.3 Hz, 1H), 7.83 (dd, J=11.0, 7.1 Hz, 1H), 3.94 (s, 3H).

Intennediate 2h: 3-(2,5-dichloropyrimidin-4-yl)-1-methyl-5-fluoro-1H-indole (Intermediate 2h)

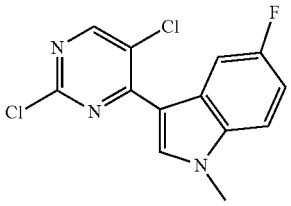

The compound was synthesized in the same manner as those in Intermediate 2a. MS m/z: 296 [M+1], 297, 298.

$^1$H NMR (400 MHz, $CDCl_3$) δ 8.49 (s, 1H), 8.46 (s, 1H), 8.46-8.42 (m, 1H), 7.34 (dd, J=8.9, 4.4 Hz, 1H), 7.14 (td, J=8.9, 2.6 Hz, 1H), 3.94 (s, 3H).

Intermediate 2i: 3-(2-chloro-5-fluoropyrimidin-4-yl)-1-methyl-1H-indole (Intermediate 2i)

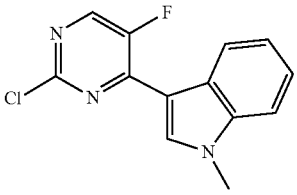

The compound was synthesized in the same manner as those in Intermediate 2a with a yield of 73%. MS m/z: 262 [M+1], 264.

$^1$H NMR (400 MHz, DMSO-d6) δ 8.69 (d, J=3.7 Hz, 1H), 8.54 (dd, J=7.2, 1.2 Hz, 1H), 8.39 (d, J=3.0 Hz, 1H), 7.62 (d, J=7.5 Hz, 1H), 7.41-7.30 (m, 2H), 3.96 (s, 3H).

Intermediate 2j: 3-(2-chloro-5-fluoropyrimidin-4-yl)-1-methyl-5-fluoro-1H-indole (Intermediate 2j)

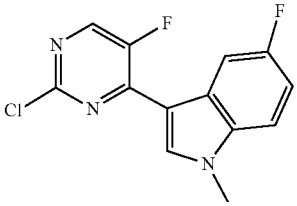

The compound was synthesized in the same manner as those in Intermediate 2a with a yield of 77%. MS m/z: 280 [M+1], 282.

$^1$H NMR (400 MHz, DMSO-d6) δ 8.71 (d, J=3.5 Hz, 1H), 8.45 (d, J=2.8 Hz, 1H), 8.20 (dd, J=10.3, 2.5 Hz, 1H), 7.66 (dd, J=8.9, 4.5 Hz, 1H), 7.30-7.16 (m, 1H), 3.96 (s, 3H).

Intermediate 2k: 3-(2-chloro-5-fluoropyrimidin-4-yl)-1-methyl-5,6-difluoro-1H-indole (Intermediate 2k)

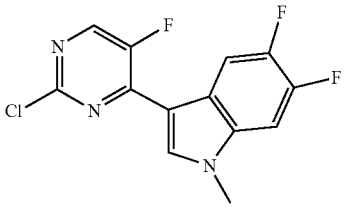

The compound was synthesized in the same manner as those in Intermediate 2a. MS m/z: 298 [M+1], 300.

$^1$H NMR (400 MHz, $CDCl_3$) δ 8.56 (dd, J=11.4, 8.1 Hz, 1H), 8.36 (d, J=3.3 Hz, 1H), 8.01 (d, J=2.6 Hz, 1H), 7.19 (dd, J=10.1, 6.6 Hz, 1H), 3.90 (s, 3H).

Intermediate 2l: 3-(2,5-dichloropyrimidin-4-yl)-1-methyl-1H-[pyrro]*pyrrolo*[2,3-b]pyridine (Intermediate 2l)

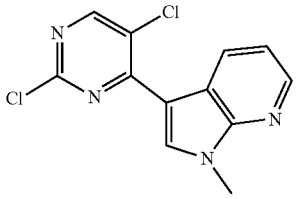

Step 1: Synthesis of 3-bromo-1-p-tosyl-1H-[pyrro]*pyrrolo*[2,3-b]pyridine

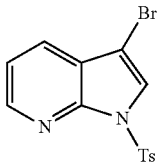

To a 250 mL three-necked flask were added 3-bromo-1H-[pyrro]*pyrrolo* [2,3-b]pyridine (4.0 g, 20.3 mmol) and 80 ml tetrahydrofuran. The mixture was cooled to below 5° C. in an ice-water bath. 60% of sodium hydride (1.3 g, 32.5 mmol) was added. The mixture was stirred for 15 minutes. p-Toluensulfonyl chloride (4.1 g, 21.3 mmol) was added. The reaction continued for 15 minutes. 150 ml water was added to quench the reaction. The reaction mixture was extracted with ethyl acetate (150 ml). The organic layer was evaporated to dryness under a reduced pressure to produce a brown solid, which was added to petroleum ether to form a shiny, and a brown solid (5 g) was obtained with a yield of 70%. MS m/z: 351 [M+1], 353.

Step 2: Synthesis of 3-(2,5-dichloropyrimidin-4-yl)-1-p-tosyl-1H-[pyrro]*pyrrolo*[2,3-b]pyridine

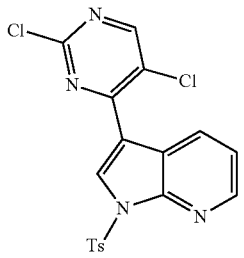

To a 100 mL single-necked flask were added 3-bromo-1-p-tosyl-1H-[pyrro]*pyrrolo*[2,3-b]pyridine (2.0 g, 5.7 mmol), bis(pinacolato)diboron (1.9 g, 7.4 mmol), potassium acetate (1.7 g, 17.1 mmol), [1,1'-Bis(diphenylphosphino)ferrocene] dichloropalladium (0.21 g, 0.285 mmol) and 25 ml dioxane with atmosphere replaced by argon. The mixture was reacted at 85° C. for 6.5 hours. LC-MS monitoring showed the starting materials were depleted. To the reaction mixture was added 2,4,5-trichloropyrimidine (1.3 g, 7.0 mmol), 5 ml 2N sodium carbonate solution and [1,1'-Bis(diphenylphosphino)ferrocene]dichloropalladium (0.37 g, 0.50 mmol) with atmosphere replaced by argon. The reaction continued at 85° C. overnight. The reaction mixture was diluted with 150 ml ethyl acetate, and washed with 150 ml water. The aqueous phase was extracted with dichloromethane (120 ml×3). The organic phases were combined, dried with anhydrous sodium sulfate, and filtered. The filtrate was evaporated to dryness under a reduced pressure, and purified by silica gel column chromatography (petroleum ether:ethyl acetate=5:1). The product was added to a mixed solvent of petroleum ether and ethyl acetate (volume ratio=2:1) to form a slurry, and 1.0 g of an off-white solid was obtained with a yield of 42%. MS m/z: 419 [M+1], 421.

Step 3: Synthesis of 3-(2,5-dichloropyrimidin-4-yl)-1H-[pyrro]*pyrrolo*[2,3-b]pyridine

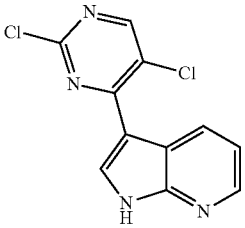

To a 100 mL single-necked flask were added 3-(2,5-dichloropyrimidin-4-yl)-1-p-tosyl-1H-[pyrro]*pyrrolo*[2,3-b]pyridine (0.95 g, 2.3 mmol) and 30 ml tetrahydrofuran. Under stirring, tetrabutylammonium fluoride (1.2 g, 4.6 mmol) was added. The mixture was reacted at room temperature for 20 minutes. To the reaction mixture was added 100 ml ethyl acetate. The reaction mixture was washed with 100 ml water. The organic phase was dried with anhydrous sodium sulfate, and filtered. The filtrate was evaporated to dryness under a reduced pressure. The residue was added to 20 ml of a mixed solvent of petroleum ether and ethyl acetate (volume ratio=4:1) to form a slurry. The slurry was filtered by suction to produce 500 mg of an off-white solid with a yield of 83%. MS m/z: 265 [M+1].

Step 4: Synthesis of 3-(2,5-dichloropyrimidin-4-yl)-1-methyl-1H-[pyrro]*pyrrolo*[2,3-b]pyridine (Intermediate 2l)

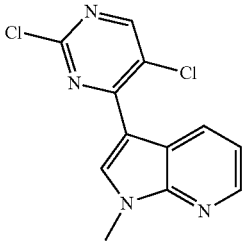

To a 50 ml three-necked flask were added 3-(2,5-dichloropyrimidin-4-yl)-1H-[pyrro]*pyrrolo*[2,3-b]pyridine (480 mg, 1.8 mmol) and 15 ml N,N-dimethylformamide. The resulting mixture was cooled to 5° C. under an ice-water bath. 60% of sodium hydride (145 mg, 3.6 mmol) was added. The mixture was stirred for 10 minutes, and methyl iodide (0.12 ml, 1.9 mmol) was added thereto. The resulting mixture was stirred at 5° C. for 15 minutes. The reaction mixture was poured to ice-water, and a solid precipitated and was filtered by suction. The filter cake was dried to produce 450 mg of [an] *a* beige solid with a yield of 89%. MS m/z: 265 [M+1].

$^1$H NMR (400 MHz, DMSO-d6) δ 8.94 (s, 1H), 8.81 (dd, J=8.0, 1.6 Hz, 1H), 8.78 (s, 1H), 8.44 (dd, J=4.7, 1.6 Hz, 1H), 7.38 (dd, J=8.0, 4.7 Hz, 1H), 3.97 (s, 3H).

Intermediate 2m: 5-(2,5-dichloropyrimidin-4-yl)-1-methyl-1H-[pyrro]*pyrrolo*[2,3-b]pyridine (Intermediate 2m)

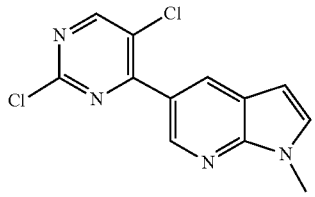

The compound was synthesized in the same manner as those in Step 2 of Intermediate 21 with a yield of 50%. MS m/z: 279 [M+1].

$^1$HNMR (400 MHz, DMSO-d6) δ 8.99 (s, 1H), 8.75 (d, J=2.1 Hz, 1H), 8.51 (d, J=2.1 Hz, 1H), 7.68 (d, J=3.5 Hz, 1H), 6.66 (d, J=3.5 Hz, 1H), 3.90 (s, 3H).

Intermediate 2n: 2,5-dichloro-4-(1-methyl-1H-pyrazol-4-yl)pyrimidine (Intermediate 2n)

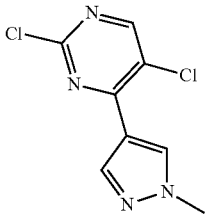

To a three-necked flask were added 2,4,5-trichloropyrimidine (2.0 g, 10.9 mmol), 1-methyl-4-pyrazole-bis(pinacolato)diboron (1.75 g, 8.4 mmol), 8.4 ml 2N sodium carbonate solution, [1,1'-Bis(diphenylphosphino)ferrocene] dichloropalladium (0.61 g, 0.84 mmol) and 30 ml dioxane with atmosphere replaced by argon. The mixture was stirred at 80° C. overnight. To the reaction mixture was added 150 ml ethyl acetate, washed successively with 150 ml water and 100 ml saturated sodium chloride solution, dried with anhydrous sodium sulfate, and evaporated to dryness under a reduced pressure to produce a earth yellow solid (1.6 g) with a yield of 83%. MS m/z: 229 [M+1].

$^1$H NMR (400 MHz, DMSO-d6) δ 8.82 (s, 1H), 8.75 (s, 1H), 8.27 (s, 1H), 3.96 (s, 3H).

Intermediate 2o: 2,5-dichloro-2'-methoxy-4,5'-bipyrimidine (Intermediate 2o)

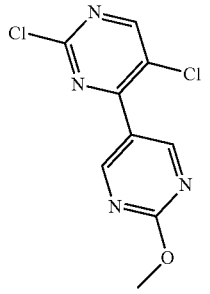

The compound was synthesized in the same manner as those in Intermediate 2n with a yield of 70%. MS m/z: 257 [M+1].

$^1$H NMR (400 MHz, DMSO-d6) δ 9.10 (s, 2H), 9.05 (s, 1H), 4.04 (s, 3H).

Intermediate 2p: 2,5-dichloro-2'-amino-4,5'-bipyrimidine (intermediate 2p)

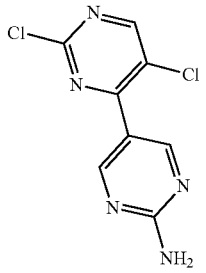

The compound was synthesized in the same manner as those in Intermediate 2n with a yield of 44%. MS m/z: 242 [M+1].

$^1$H NMR (400 MHz, DMSO-d6) δ 8.90 (s, 1H), 8.84 (s, 2H), 7.52 (s, 2H).

Example 1: N-{2-{[2-(dimethylamino)ethyl](methy)amino}-6-isopropyloxy-5-{5-chloro-[4-(1-methyl-1H-indol-3-yl)pyrimidin-2-yl]amino}pyridin-3-yl}acrylamide

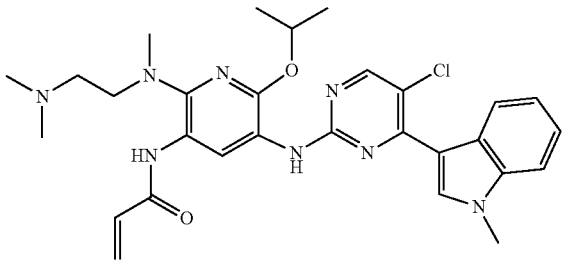

Step 1: Synthesis of $N^2$-methyl-$N^2$-[2-(dimethylamino)ethyl]-6-isopropyloxy-$N^5$ [5-chloro-4-(1-methyl-1H-indol-3-yl)pyrimidin-2-yl]-3-nitropyridin-2,5-diamine

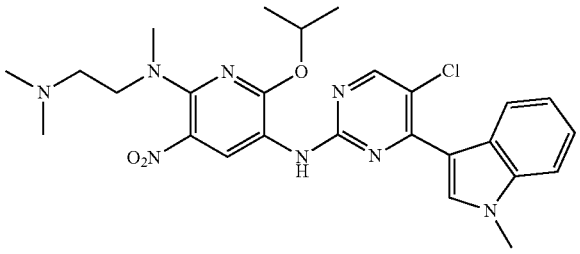

To a 50 mL single-necked flask were added $N^2$-methyl-$N^2$-[2-(dimethylamino)ethyl]-6-isopropyloxy-3-nitropyridin-2,5-diamine (490 mg, 1.65 mmol), 3-(2,5-dichloropyrimidin-4-yl)-1-methyl-1H-indole (550 mg, 1.98 mmol), tris(dibenzylideneacetone)dipalladium (226 mg, 0.2475 mmol), 4,5-Bis(diphenylphosphino)-9,9-dimethylxanthene (286 mg, 0.495 mmol), potassium phosphate (874 mg, 4.125 mmol) and 15 ml dioxane. Under the nitrogen protection, the mixture was reacted at 100° C. overnight. The reaction mixture was filtered with diatomite. The filtrate was evaporated to dryness under a reduced pressure, purified by silica gel column chromatography (dichloromethane:methanol=50:1) to produce 480 mg of a product with a yield of 54%. MS in/z: 539 [M+1].

Step 2: Synthesis of $N^2$-methyl-$N^2$-[2-(dimethylamino)ethyl]-6-isopropyloxy-$N^5$-[5-chloro-4-(1-methyl-1H-indol-3-yl)pyrimidin-2-yl]pyridin-2,3,5-triamine

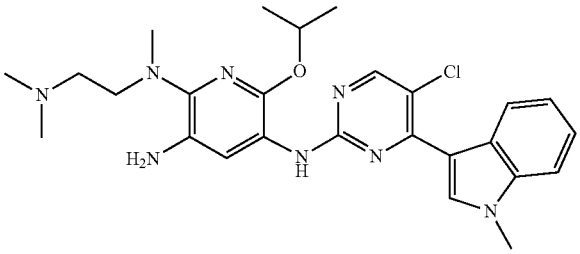

To a 50 mL single-necked flask were added $N^2$-methyl-$N^2$-[2-(dimethylamino)ethyl]-6-isopropyloxy-$N^5$-[5-chloro-4-(1-methyl-1H-indol-3-yl)pyrimidin-2-yl]-3-nitropyridin-2,5-diamine (480 mg, 0.892 mmol), ammonia chloride (48 mg, 0.897 mmol) and 12 ml of a mixed solvent of ethanol and water (volume ratio=3:1). To the mixture was added in batch a reduced iron powders (240 mg, 4.26 mmol). The mixture was stirred at 80° C. for 1 hour. The reaction mixture was cooled to room temperature, and filtered through diatomite. The filtrate was evaporated to dryness under a reduced pressure, dissolved in dichloromethane, and washed with a saturated sodium carbonate solution. The organic layer was dried with anhydrous sodium sulfate and filtered. The filtrate was evaporated to dryness under a reduced pressure, and subjected to a preparative TLC separation (dichloromethane:ethyl acetate:methanol=5:5:1) to produce 96 mg of a product with a yield of 43%. MS m/z: 509 [M+1].

Step 3: Synthesis of N-{2-{[2-(dimethylamino)ethyl](methyl)amino}-6-isopropyloxy-5-{5-chloro-[4-(1-methyl-1H-indol-3-yl)pyrimidin-2-yl]amino}pyridin-3-yl}acrylamide

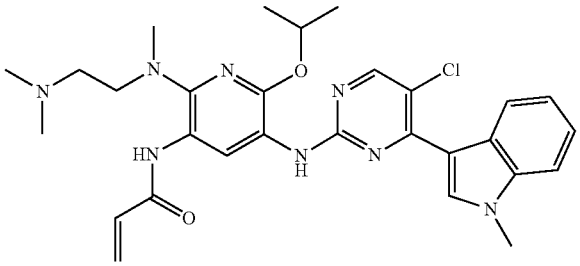

To a 50 ml single-necked flask were added $N^2$-methyl-$N^2$-[2-(dimethylamino)ethyl]-6-isopropyloxy-$N^5$-[5-chloro-4-(1-methyl-1H-indol-3-yl)pyrimidin-2-yl]pyridin-2,3,5-triamine (196 mg, 0.385 mmol) and 10 ml dichloromethane. The reaction mixture was cooled in an ice-water bath. 0.5 N of a solution of acryloyl chloride in dichloromethane (0.8 ml, 0.4 mmol) and triethylamine (0.15 ml, 1.08 mmol) were added. The mixture was reacted at room temperature for 0.5 hour. To the reaction mixture was added a suitable amount of water. The dichloromethane layer was separated, dried with anhydrous sodium sulfate, and filtered. The filtrate was concentrated under a reduced pressure, and purified by preparative TLC separation (dichloromethane:ethyl acetate:methano=5:5:1) to produce 130 mg of a pale-yellow solid with a yield of 60%. MS m/z: 563 [M+1], 565.

$^1$H NMR (400 MHz, $CDCl_3$) δ 9.75 (s, 1H), 9.36 (s, 1H), 8.39 (s, 1H), 8.38-8.33 (m, 1H), 8.29 (s, 1H), 7.40 (s, 1H), 7.38-7.33 (m, 1H), 7.33-7.27 (m, 2H), 7.06 (dd, J=16.9, 10.2 Hz, 1H), 6.39 (d, J=16.9 Hz, 1H), 5.70 (d, J=10.2 Hz, 1H), 5.29-5.20 (m, 1H), 3.90 (s, 3H), 3.51-3.46 (m, 2H), 3.09 (br s, 2H), 2.77 (s, 3H), 2.75 (s, 6H), 1.38 (d, J=6.2 Hz, 6H).

Example 2: N-{2-{[2-(dimethylamino)ethyl](methyl)amino}-6-isopropyloxy-5-{[4-(1-methyl-1H-indol-3-yl)pyrimidin-2-yl]amino}pyridin-3-yl}acrylamide

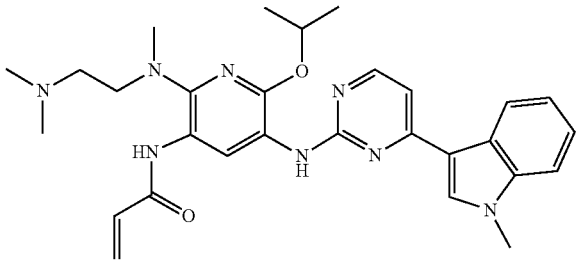

Step 1: Synthesis of $N^2$-methyl-$N^2$-[2-(dimethylamino)ethyl]-6-isopropyloxy-$N^5$-[4-(1-methyl-1H-indol-3-yl)pyrimidin-2-yl]-3-nitropyridin-2,5-diamine

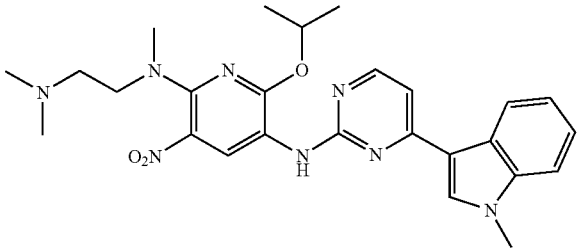

The compound was synthesized in the same manner as those in Step 1 of Example 1 with a yield of 100%.

Step 2: Synthesis of $N^2$-methyl-$N^2$-[2-(dimethylamino)ethyl]-6-isopropylory-$N^5$-[4-(1-methyl-1H-indol-3-yl)pyrimidin-2-yl]pyridin-2,3,5-triamine

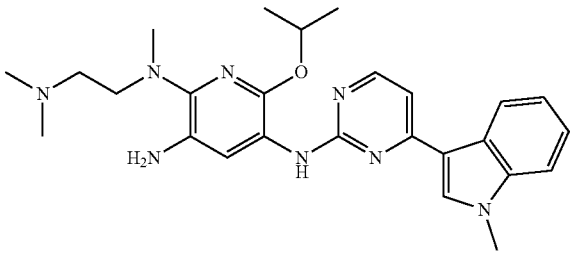

$N^2$-methyl-$N^2$-[2(dimethylamino)ethyl]-6-isopropyloxy-$N^5$-[4-(1-methyl-1H-indol-3-yl)pyrimidin-2-yl]-3-nitropyridin-2,5-diamine (200 mg, 0.397 mmol) was dissolved in 12 ml methanol. 35 mg platinum dioxide was added and hydrogen was introduced. The resulting mixture was stirred at room temperature for 1.5 hour, and filtered. The filtrate was concentrated under a reduced pressure, and subjected to a preparative TLC seperation (dichloromethane:ethyl acetate:methanol=9:1:1) to produce 50 mg of a product with a yield of 27%. MS m/z: 475 [M+1].

Step 3: Synthesis of N-{2-{[2-(dimethylamino)ethyl](methyl)amino}-6-isopropyloxy-5-{[4-(1-methyl-1H-indol-3-yl)pyrimidin-2-yl]amino}pyridin-3-yl}acrylamide

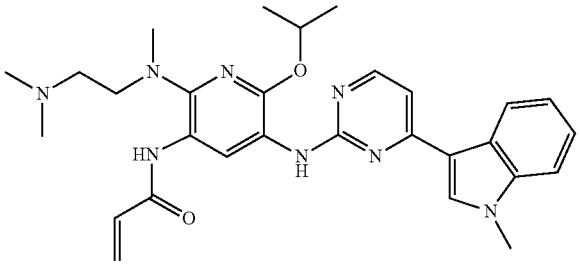

The compound was synthesized in the same manner as those in Step 3 of Example 1 with a yield of 45%. MS m/z: 529 [M+1].

$^1$H NMR (400 MHz, $CDCl_3$) δ 9.80 (s, 1H), 9.73 (s, 1H), 8.88 (s, 1H), 8.39 (d, J=5.3 Hz, 1H), 8.11-8.03 (m, 1H), 7.81 (d, J=8.3 Hz, 1H), 7.48 (s, 1H), 7.42-7.40 (m, 1H), 7.36 (d, J=8.1 Hz, 1H), 7.30 (d, J=3.7 Hz, 1H), 7.24 (d, J=5.3 Hz, 1H), 6.50 (dd, J=16.9, 1.9 Hz, 1H), 5.76 (dd, J=10.2, 1.9 Hz, 1H), 5.32-5.21 (m, 1H), 3.99 (s, 3H), 3.52 (br s, 2H), 3.11 (br s, 2H), 2.81 (d, J=2.5 Hz, 9H), 1.39 (d, J=6.2 Hz, 6H).

Example 3: N-{2-{[2-(dimethylamino)ethyl](methyl)amino}-6-(2,2,2-trifluoroethoxyl)-5-{[4-(1-methyl-1H-indol-3-yl)pyrimidin-2-yl]amino}pyridin-3-yl}acrylamide

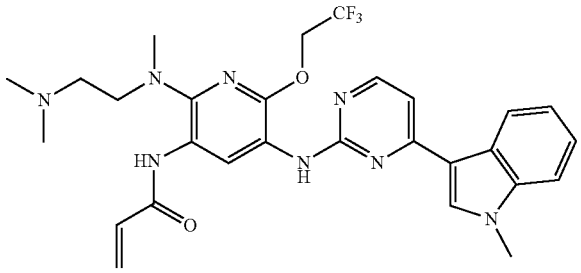

Step 1: Synthesis of $N^2$-methyl-$N^2$-[2-(dimethylamino)ethyl]-6-(2,2,2-trifluoroethoxyl)-$N^5$-[4-(1-methyl-1H-indol-3-yl)pyrimidin-2-yl]-3-nitropyridin-2,5-diamine

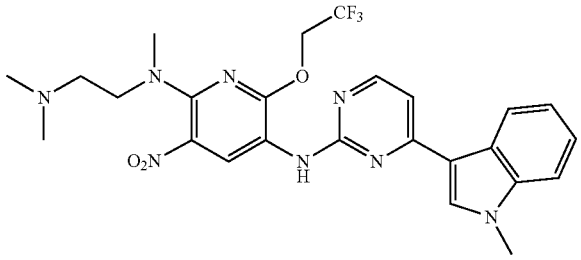

The compound was synthesized in the same manner as those in Step 1 of Example 1 with a yield of 86%. MS m/z: 545 [M+1].

Step 2: Synthesis of $N^2$-methyl-$N^2$-[2-(dimethylamino)ethyl]-6-(2,2,2-trifluoroethoxyl)-$N^5$-[4-(1-methyl-1H-indol-3-yl)pyrimidin-2-yl]pyridin-2,3,5-triamine

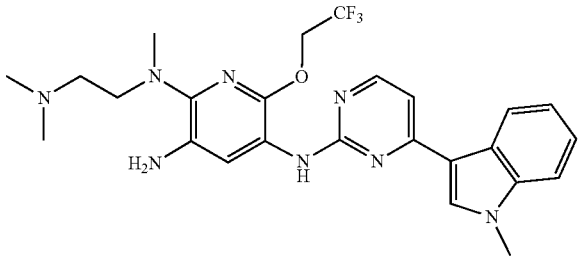

The compound was synthesized in the same manner as those in Step 2 of Example 2 with a yield of 56%. MS m/z: 515 [M+1].

Step 3: Synthesis of N-{2-{[2-(dimethylamino)ethyl](methyl)amino}-6-(2,2,2-trifluoroethoxyl)-5-{[4-(1-methyl-1H-indol-3-yl)pyrimidin-2-yl]amino}pyridin-3-yl}acrylamide

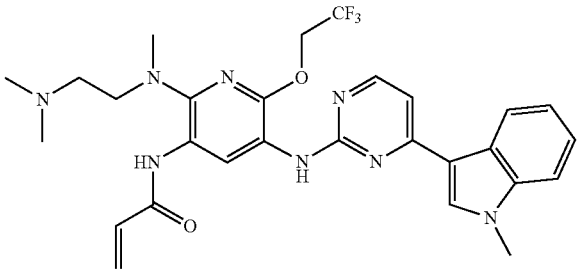

The compound was synthesized in the same manner as those in Step 3 of Example 1 with a yield of 23%. MS m/z: 569 [M+1].

$^1$H NMR (400 MHz, DMSO-d6) δ 10.41 (s, 1H), 10.27 (s, 1H), 8.68 (s, 1H), 8.44 (s, 1H), 8.28 (t, J=8.5 Hz, 2H), 8.18 (s, 1H), 7.52 (d, J=8.0 Hz, 1H), 7.29-7.14 (m, 3H), 6.98 (s, 1H), 6.28 (d, J=17.1 Hz, 1H), 5.76 (d, J=10.4 Hz, 1H), 5.00 (q, J=9.0 Hz, 2H), 3.89 (s, 3H), 3.61 (s, 2H), 3.28 (s, 2H), 2.80 (s, 3H), 2.73 (s, 6H).

Example 4: N-{2-{[2-(dimethylamino)ethyl](methyl)amino}-6-(2,2,2-trifluoroethoxyl)-5-{5chloro-[4-(1-methyl-1H-indol-3-yl)pyrimidin-2-yl]amino}pyridin-3-yl}acrylamide

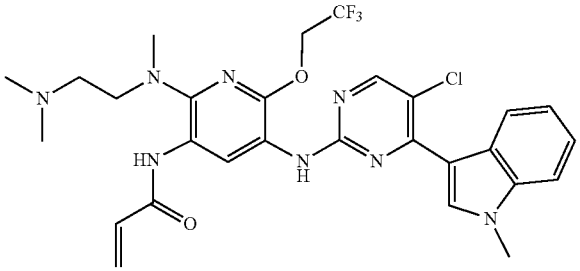

Step 1: Synthesis of $N^2$-methyl-$N^2$-[2-(dimethylamino)ethyl]-6-(2,2,2-trifluoroethoxyl)-$N^5$-[5-chloro-4-(1-methyl-1H-indol-3-yl)pyrimidin-2-yl]-3-nitropyridin-2,5-diamine

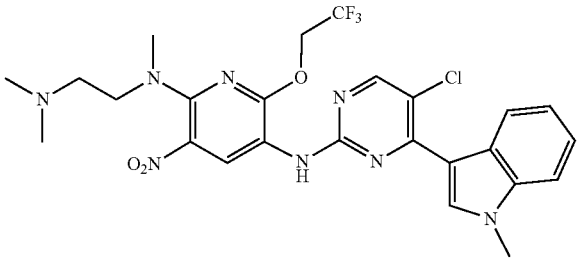

The compound was synthesized in the same manner as those in Step 1 of Example 1 with a yield of 86%.

Step 2: Synthesis of $N^2$-methyl-$N^2$-[2-(dimethylamino)ethyl]-6-(2,2,2-trifluoroethoxyl)-$N^5$-[5-chloro-4-(1-methyl-1H-indol-3-yl)pyrimidin-2-yl]pyridin-2,3,5-triamine

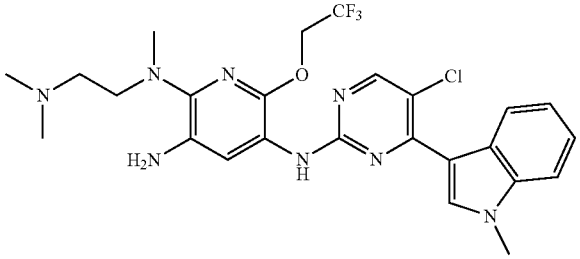

The compound was synthesized in the same manner as those in Step 2 of Example 1 with a yield of 65%.

Step 3: Synthesis of N-{2-{[2-(dimethylamino)ethyl](methyl)amino}-6-(2,2,2-trifluoroethoxyl)-5-{5-chloro-[4-(1-methyl-1H-indol-3-yl)pyrimidin-2-yl]amino}pyridin-3-yl}acrylamide

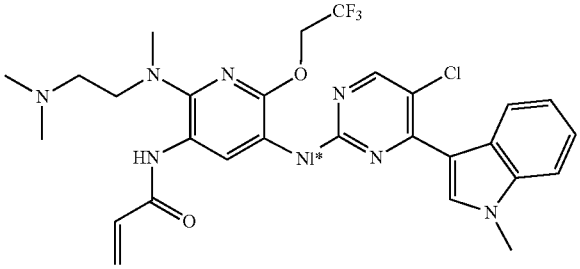

The compound was synthesized in the same manner as those in Step 3 of Example 1 with a yield of 15%. MS m/z: 603 [M+1], 605.

$^1$H NMR (400 MHz, $CDCl_3$) δ 11.68 (br s, 1H), 9.77 (s, 1H), 9.48 (s, 1H), 8.42 (s, 1H), 8.38 (d, J=8.7 Hz, 1H), 8.33 (s, 1H), 7.40-7.37 (m, 2H), 7.32 (dd, J=6.7, 3.0 Hz, 2H), 7.12 (dd, J=16.8, 10.2 Hz, 1H), 6.43 (dd, J=16.9, 1.8 Hz, 1H), 5.72 (dd, J=10.2, 1.8 Hz, 1H), 4.83 (q, J=8.4 Hz, 2H), 3.93 (s, 3H), 3.60 (s, 2H), 3.17 (s, 2H), 2.86 (s, 3H), 2.85 (s, 6H).

Example 5: N-{2-{[2-(dimethylamino)ethyl](methyl)amino}-6-isopropyloxy-5-{[4-(1-methyl-5-fluoro-1H-indol-3-yl)pyrimidin-2-yl]amino}pyridin-3-yl}acrylamide

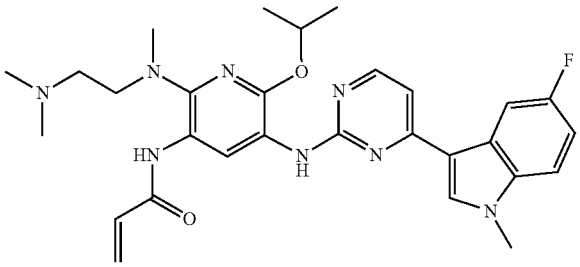

Step 1: Synthesis of $N^2$-methyl-$N^2$-[2(dimethylamino)ethyl]-6-isopropyloxy-$N^5$-[4-(1-methyl-5-fluoro-1H-indol-3-yl)pyrimidin-2-yl]-3-nitropyridin-2,5-diamine

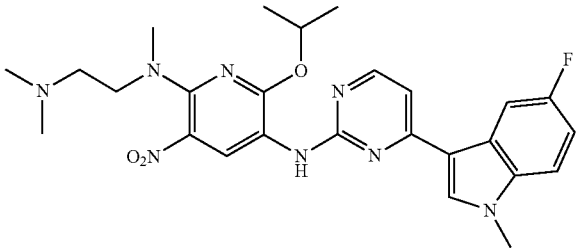

The compound was synthesized in the same manner as those in Step 1 of Example 1 with a yield of 57%. MS m/z: 523.

Step 2: Synthesis of $N^2$-methyl-$N^2$-[2(dimethylamino)ethyl]-6-isopropyloxy-$N^5$-[4-(1-methyl-5-fluoro-1H-indol-3-yl)pyrimidin-2-yl]pyridin-2,3,5-triamine

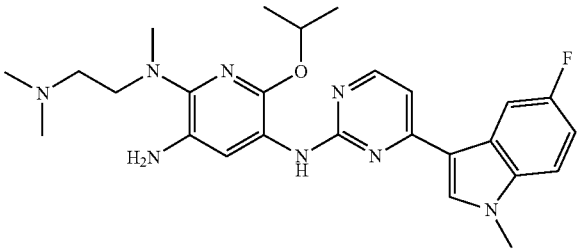

The compound was synthesized in the same manner as those in Step 2 of Example 1 with a yield of 64%. MS m/z: 493 [M+1].

Step 3: Synthesis of N-{2-{[2-(dimethylamino)ethyl](methy)amino}-6-isopropyloxy-5-{[4-(1-methyl-5-fluoro-1H-indol-3-yl)pyrimidin-2-yl]amino}pyridin-3-yl}acrylamide

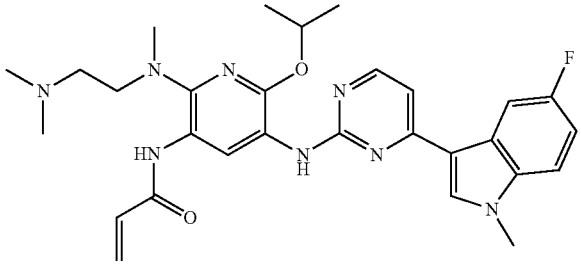

The compound was synthesized in the same manner as those in Step 3 of Example 1 with a yield of 45%. MS m/z: 547 [M+1].

$^1$H NMR (400 MHz, $CDCl_3$) δ 9.82 (s, 1H), 9.80 (s, 1H), 8.93 (s, 1H), 8.40 (d, J=5.2 Hz, 1H), 7.71 (d, J=9.7 Hz, 1H), 7.49 (s, 1H), 7.32 (dd, J=8.8, 4.4 Hz, 1H), 7.20-6.98 (m, 3H), 6.48 (d, J=16.8 Hz, 1H), 5.76 (d, J=10.5 Hz, 1H), 5.31-5.25 (m, 1H), 3.99 (s, 3H), 3.43 (br s, 2H), 2.98 (br s, 2H), 2.71 (s, 6H), 1.39 (d, J=6.1 Hz, 6H).

Example 6: N-{2-{[2-(dimethylamino)ethyl](methyl)amino}-6-isopropyloxy-5-{[4-(1-methyl-5,6-difluoro-1H-indol-3-yl)pyrimidin-2-yl]amino}pyridin-3-yl}acrylamide

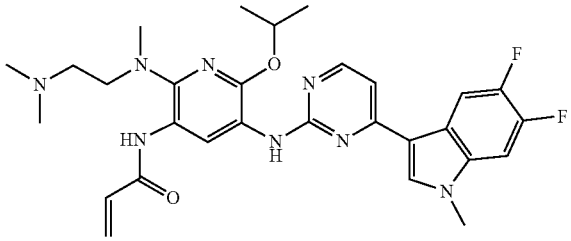

Step 1: Synthesis of $N^2$-methyl-$N^2$-[2-(dimethylamino)ethyl]-6-isopropyloxy-$N^5$-[4-(1-methyl-5,6-difluoro-1H-indol-3-yl)pyrimidin-2-yl]-3-nitropyridin-2,5-diamine

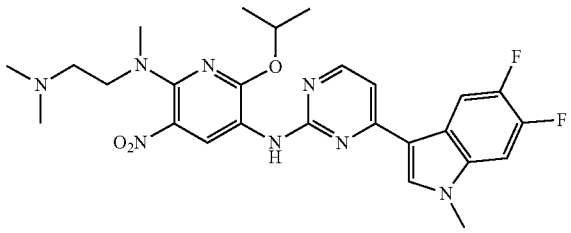

The compound was synthesized in the same manner as those in Step 1 of Example 1 with a yield of 28%. MS m/z: 541.

Step 2: Synthesis of $N^2$-methyl-$N^2$-[2-(dimethylamino)ethyl]-6-isopropyloxy-$N^5$-[4-(1-methyl-5,6-difluoro-1H-indol-3-yl)pyrimidin-2-yl]pyridin-2,3,5-triamine

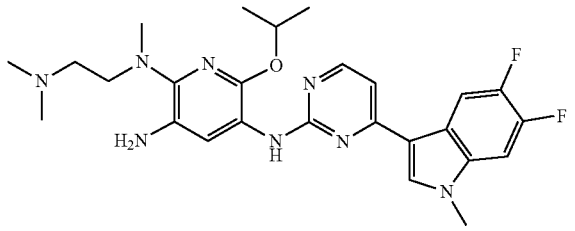

The compound was synthesized in the same manner as those in Step 2 of Example 1 with a yield of 64%. MS m/z: 511 [M+1].

Step 3: Synthesis of N-{2-{[2-(dimethylamino)ethyl](methyl)amino}-6-isopropyloxy-5-{[4-(1-methyl-5,6-difluoro-1H-indol-3-yl)pyrimidin-2-yl]amino}pyridin-3 -yl}acrylamide

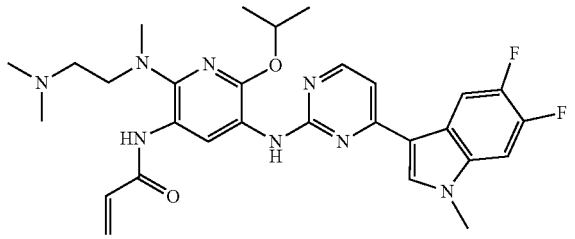

The compound was synthesized in the same manner as those in Step 3 of Example 1 with a yield of 38%. MS m/z: 565 [M+1].

$^1$H NMR (400 MHz, $CDCl_3$) δ 9.73 (s, 1H), 9.70 (s, 1H), 8.82 (s, 1H), 8.39 (d, J=4.9 Hz, 1H), 7.88-7.74 (m, 1H), 7.50 (s, 1H), 7.25 (dd, J=16.2, 9.7 Hz, 1H), 7.20-7.13 (m, 1H), 7.05 (d, J=5.0 Hz, 1H), 6.47 (d, J=16.5 Hz, 1H), 5.76 (d, J=10.3 Hz, 1H), 5.31-5.21 (n, 1H), 3.94 (s, 3H), 3.54 (s, 2H), 3.13 (s, 2H), 2.82 (s, 6H), 1.39 (d, J=5.9 Hz, 6H).

Example 7: N-{2-{[2-(dimethylamino)ethyl](methyl)amino}-6-isopropyloxy-5-{5-chloro-[4-(1-methyl-6-fluoro-1H-indol-3-yl)pyrimidin-2-yl]amino}pyridin-3-yl}acrylamide

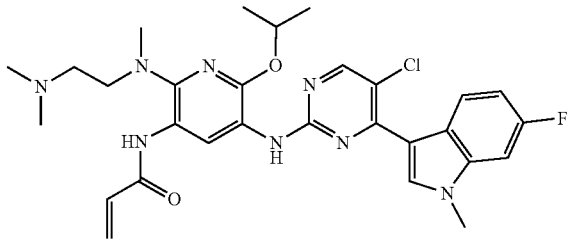

To a 25 ml three-necked flask were added tert-butyl {5-acrylamide-6-{[2-(dimethylamino)ethyl](methyl)amino}-2-isopropyloxypyridin-3-yl}carbamate (160 mg, 0.38 mmol), 3-(2,5-dichloropyrimidin-4-yl)-6-fluoro-1-methyl-1H-indole (112 mg, 0.38 mmol), p-toluenesulfonic acid monohydrate (112 mg, 0.59 mmol), 4 ml 2-amyl alcohol and 2 ml N-methylpyrrolidone. Under the nitrogen protection, the mixture was reacted at 120° C. overnight. The mixture was cooled to room temperature and poured into 50 ml water. A solid precipitated and was filtered. The solid was dissolved in 20 ml dichloromethane, washed successively with 10 ml saturated sodium bicarbonate solution and 10 ml water, dried with anhydrous sodium sulfate, and filtered. The filtrate was evaporated to dryness under a reduced pressure, and subjected to a preparative TLC seperation (dichloromethane:methanol=10:1).

$^1$H NMR (400 MHz, $CDCl_3$) δ 9.78 (s, 1H), 9.46 (s, 1H), 8.43 (s, 1H), 8.32-8.28 (m, 2H), 7.40 (s, 1H), 7.08-7.03 (m, 2H), 7.00-6.86 (m, 1H), 6.45-6.38 (m, 1H), 5.73 (d, J=10.2 Hz, 1H), 5.31-5.23 (m, 1H), 3.88 (s, 3H), 3.45 (s, 2H), 2.99 (s, 2H), 2.80 (s, 3H), 2.73 (s, 6H), 1.39 (d, J=6.2 Hz, 6H).

Example 8: N-{2-{[2-(dimethylamino)ethyl](methyl)amino}-6-isopropyloxy-5-{5-chloro-[4-(1-methyl-5,6-difluoro-1H-indol-3-yl)pyrimidin-2-yl]amino}pyridin-3-yl}acrylamide

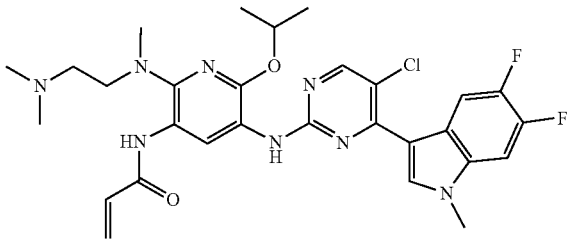

The compound was prepared in the same manner as those in Example 7 with a yield of 8%. MS m/z: 599 [M+1].

$^1$H NMR (400 MHz, DMSO-d6) δ 9.93 (s, 1H), 8.71 (s, 1H), 8.66 (s, 1H), 8.37 (s, 1H), 8.25 8.15 (n, 1H), 8.11 (s, 1H), 7.68 (dd, J=11.1, 7.0 Hz, 1H), 6.83-6.64 (m, 1H), 6.21 (d, J=16.5 Hz, 1H), 5.73 (d, J=11.9 Hz, 1H), 5.21 5.13 (m, 1H), 3.89 (s, 3H), 3.36 (s, 4H), 2.80 (s, 3H), 2.56 (s, 6H), 1.18 (d, J=6.1 Hz, 6H).

Example 9: N-{2-{[2-(dimethylamino)ethyl](methyl)amino}-6-isopropyloxy-5-{5-chloro-[4-(1-methyl-5-fluoro-1H-indol-3-yl)pyrimidin-2-yl]atnino}pyridin-3-yl}acrylamide

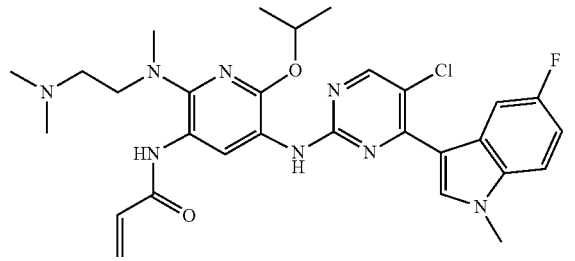

The compound was prepared in the same manner as those in Example 7 with a yield of 10%. MS m/z: 581 [M+1].

$^1$H NMR (400 MHz, MeOD) δ 8.48 (s, 1H), 8.36 (s, 1H), 8.34 (s, 1H), 8.02 (dd, J=10.6, 2.4 Hz, 1H), 7.44 (dd, J=8.9, 4.4 Hz, 1H), 7.03 (td, J=9.0, 2.5 Hz, 1H), 6.47 (dd, J=17.0, 9.3 Hz, 1H), 6.40 (dd, J=17.0, 2.5 Hz, 1H), 5.82 (dd, J=9.3, 2.5 Hz, 1H), 5.39-5.28 (m, 1H), 3.91 (s, 3H), 3.74 (t, J=5.7 Hz, 2H), 3.32 (t, J=5.9 Hz, 2H), 2.89 (s, 6H), 2.80 (s, 3H), 1.37 (d, J=6.2 Hz, 6H).

Example 10: N-{-2-{[2-(dimethylamino)ethyl](methy)amino}-6-isopropyloxy-5-{5-fluoro-[4-(1-methyl-5-fluoro-1H-indol-3-yl)pyrimidin-2-yl]amino}pyridin-3-yl}acrylamide

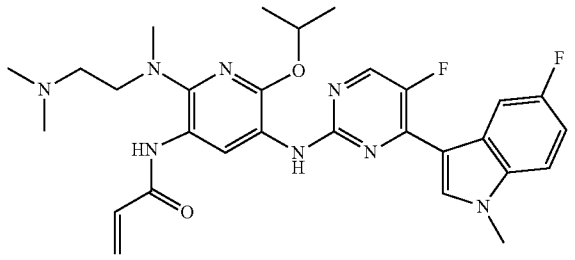

The compound was prepared in the same manner as those in Example 7 with a yield of 9%. MS m/z: 565 [M+1].

$^1$H NMR (400 MHz, DMSO-d6) δ 10.01 (s, 1H), 8.45 (s, 1H), 8.35 (d, J=3.9 Hz, 1H), 8.28 (d, J=2.7 Hz, 1H), 8.26 (s, 1H), 8.07 (d, J=10.2 Hz, 1H), 7.55 (dd, J=8.9, 4.6 Hz, 1H), 7.11 (td, J=9.1, 2.6 Hz, 1H), 6.90 (s, 1H), 6.23 (dd, J=17.1, 1.9 Hz, 1H), 5.72 (dd, J=10.2, 1.9 Hz, 1H), 5.26-5.12 (m, 1H), 3.92 (s, 3H), 3.53 (s, 2H), 3.24 (s, 2H), 2.77 (s, 3H), 2.71 (s, 6H), 1.21 (d, J=6.2 Hz, 6H).

Example 11: N-{2-{[2-(dimethylamino)ethyl](methy)amino}-6-isopropyloxy-5-{5-fluoro-[4-(1-methyl-1H-indol-3-yl)pyrimidin-2-yl]amino}pyridin-3-yl}acrylamide

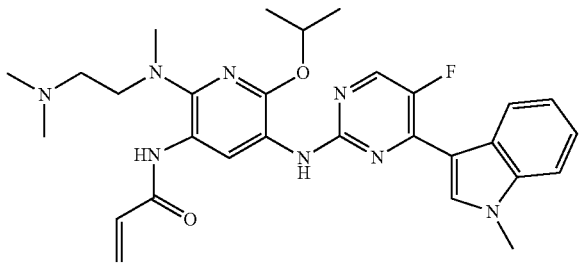

The compound was prepared in the same manner as those in Example 7 with a yield of 7%. MS m/z: 547 [M+1].

$^1$H NMR (400 MHz, DMSO-d6) δ 10.12 (s, 1H), 8.47 8.32 (m, 3H), 8.23 (d, J=2.8 Hz, 1H), 8.19 (s, 1H), 7.52 (d, J=8.2 Hz, 1H), 7.24 (t, J=7.6 Hz, 1H), 7.15 (t, J=7.5 Hz, 1H), 6.88 (dd, J=16.9, 10.3 Hz, 1H), 6.23 (dd, J=17.1, 1.8 Hz, 1H), 5.72 (dd, J=10.2, 1.7 Hz, 1H), 5.27-5.15 (m, 1H), 4.04 (s, 3H), 3.91 (s, 3H), 3.57 (s, 2H), 3.28 (s, 2H), 2.76 (s, 6H), 1.26 (d, J=6.2 Hz, 6H).

Example 12: N-{2-{[2-(dimethylamino)ethyl](methyl)amino}-6-isopropyloxy-5-{5-fluoro-[4-(1-methyl-5,6-difluoro-1H-indol-3-yl)pyrimidin-2-yl]amino}pyridin-3-yl}acrylamide

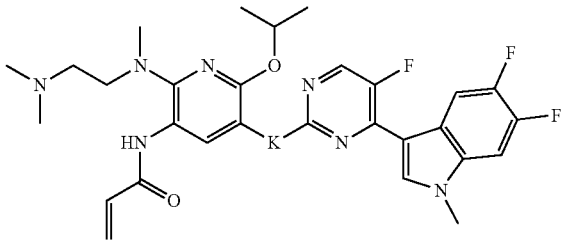

The compound was prepared in the same manner as those in Example 7. MS m/z: 583 [M+1].

$^1$H NMR (400 MHz, $CDCl_3$) δ 9.70 (s, 1H), 9.47 (s, 1H), 8.29 (d, J=3.4 Hz, 2H), 8.23 (dd, J=11.8, 8.2 Hz, 1H), 7.33 (s, 1H), 7.14 (dd, J=10.3, 6.7 Hz, 2H), 6.41 (dd, J=16.9, 1.8 Hz, 1H), 5.73 (dd, J=10.2, 1.8 Hz, 1H), 5.31-5.23 (m, 1H), 3.90 (s, 3H), 3.55 (s, 2H), 3.13 (s, 2H), 2.83 (s, 9H), 1.40 (d, J=6.2 Hz, 6H).

Example 13: N-{2-{[2-(dimethylamino)ethyl](methyl)amino}-6-isopropyloxy-5-{[4-(1-methyl-6-fluoro-1H-indol-3-yl)pyrimidin-2-yl]amino}pyridin-3-yl}acrylaimide

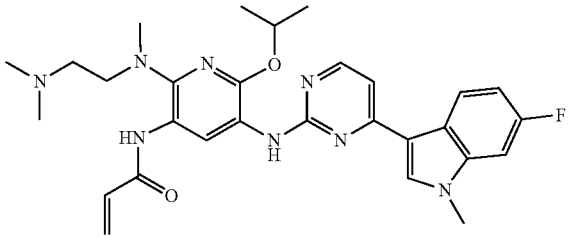

The compound was prepared in the same manner as those in Example 7 with a yield of 15%. MS m/z: 547 [M+1].

$^1$H NMR (400 MHz, $CDCl_3$) δ 9.77 (s, 1H), 9.76 (s, 1H), 8.82 (s, 1H), 8.39 (d, J=5.3 Hz, 1H), 7.98 (dd, J=8.7, 5.2 Hz, 1H), 7.47 (s, 1H), 7.16 (d, J=5.3 Hz, 1H), 7.08 (dd, J=9.6, 2.3 Hz, 1H), 7.03 (dd, J=9.1, 2.2 Hz, 1H), 6.49 (dd, J=16.9, 2.0 Hz, 1H), 5.77 (dd, J=10.2, 2.0 Hz, 1H), 5.27 (hept, J=6.2 Hz, 1H), 3.94 (s, 3H), 3.52 (s, 2H), 3.10 (s, 2H), 2.82 (s, 3H), 2.80 (s, 6H), 1.39 (d, J=6.2 Hz, 6H).

Example 14: N-{2-{[2-(dimethylamino)ethyl](methyl)amino}-6-(2,2,2-trifluoroethoxyl)-5-{5-fluoro-[4-(1-methyl-1H-indol-3-yl)pyrimidin-2-yl]amino}pyridin-3-yl}acrylamide

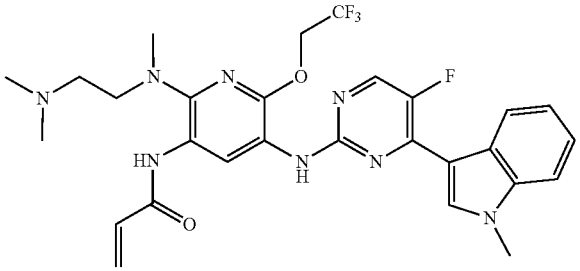

The compound was prepared in the same manner as those in Example 7. MS m/z: 587 [M+1].

$^1$H NMR (400 MHz, $CDCl_3$) δ 9.87 (s, 1H), 9.53 (s, 1H), 8.52-8.44 (m, 1H), 8.28 (d, J=3.7 Hz, 1H), 8.21 (s, 1H), 7.38 (dd, J=8.1, 4.9 Hz, 1H), 7.33 (dd, 1=6.0, 3.3 Hz, 2H), 7.19 (dd, J=16.9, 10.3 Hz, 1H), 6.43 (dd, J=16.9, 1.5 Hz, 1H), 5.74 (dd, J=10.3, 1.5 Hz, 1H), 4.83 (q, J=8.5 Hz, 2H), 3.93 (s, 3H), 3.56 (t, J=5.1 Hz, 2H), 3.15 (t, J=5.1 Hz, 2H), 2.85 (s, 3H), 2.81 (s, 6H).

Example 15: N-{2-{[2-(dimethylamino)ethyl](methyl)amino}-6-(2,2,2-trifluoroethoxyl)-5-{[4-(1-methyl-5-fluoro-1H-indol-3-yl)pyrimidin-2-yl]amino}pyridin-3-yl}acrylamide

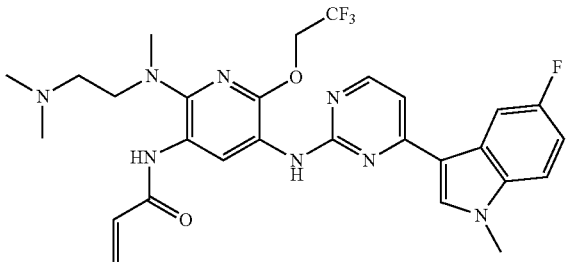

The compound was prepared in the same manner as those in Example 7. MS m/z: 587 [M+1].

$^1$H NMR (400 MHz, $CDCl_3$) δ 9.85 (s, 2H), 8.83 (s, 1H), 8.40 (d, J=5.3 Hz, 1H), 7.71 (dd, J=10.2, 2.1 Hz, 1H), 7.41 (s, 1H), 7.31 (dd, J=8.9, 4.5 Hz, 1H), 7.13 (d, J=5.3 Hz, 2H), 7.03 (td, J=9.0, 2.3 Hz, 1H), 6.49 (dd, J=16.9, 1.8 Hz, 1H), 5.78 (dd, J=10.2, 1.8 Hz, 1H), 4.83 (q, J=8.5 Hz, 2H), 3.97 (s, 3H), 3.49 (s, 2H), 3.05 (s, 2H), 2.83 (s, 3H), 2.75 (s, 6H).

Example 16: N-{2-{[2-(dimethylamino)ethyl](methyl)amino}-6-isopropyloxy-5-{5-chloro-[4-(1-methyl-1H-indol-3-yl)pyrimidin-2-yl]amino}pyridin-3-yl}acrylamide methanesulfonate

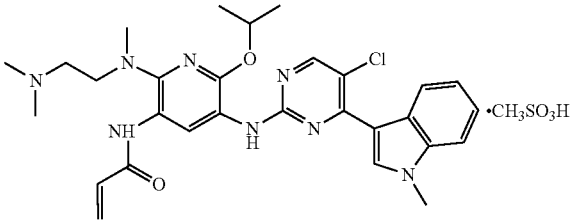

To N-{2-{[2-(dimethylamino)ethyl](methyl)amino}-6-isopropyloxy-5-{5-chloro-[4-(1-methyl-1H-indol-3-yl)pyrimidin-2-yl]amino}pyridin-3-yl}acrylamide (56 mg, 0.1 mmol) were added 2 ml acetone, 0.4 ml water, and methanesulfonic acid (6.5 μl, 0.1 mmol). The mixture was heated at 50° C. to be completely dissolved, and evaporated to dryness under a reduced pressure. Acetonitrile was added, and the resulting mixture was again evaporated to dryness under a reduced pressure. Acetone was added to the residue, and the resulting mixture was ultrasonically treated and filtered. The filter cake was dried to produce 40 mg of a yellow solid with a yield of 61%.

$^1$H NMR (400 MHz, DMSO-d6) δ 9.99 (s, 1H), 9.88 (s, 1H), 8.63 (s, 2H), 8.40 (s, 1H), 8.28 (s, 1H), 8.19 (s, 1H), 7.52 (d, J=7.3 Hz, 1H), 7.25 (s, 1H), 7.10 (s, 1H), 6.88-6.70 (m, 1H), 6.26 (d, J=16.8 Hz, 1H), 5.75 (d, J=8.6 Hz, 1H), 5.18 (br s, 1H), 3.92 (s, 3H), 3.46 (s, 2H), 3.31 (s, 2H), 2.79 (s, 9H), 2.38 (s, 3H), 1.32-1.12 (m, 6H).

Example 17: N-{2-{[2-(dimethylamino)ethyl](methyl)amino}-6-isopropyloxy-5-{5-chloro-[4-(1-methyl-5,6-difluoro-1H-indol-3-yl)pyrimidin-2-yl]amino}pyridin-3-yl}acrylamide methanesulfonate

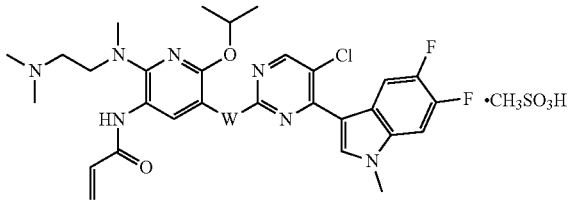

The compound was synthesized in the substantially same manner as those in Example 16. Ethyl acetate was added to the final crude product. The mixture was ultrasonically treated and filtered to produce a product with a yield of 43%.

$^1$H NMR (400 MHz, DMSO-d6) δ 10.02 (s, 1H), 9.95 (s, 1H), 8.90 (s, 1H), 8.71 (s, 1H), 8.39 (s, 1H), 8.21 (s, 1H), 8.09 (s, 1B), 7.69 (dd, J=11.1, 7.0 Hz, 1H), 6.84 (dd, J=17.0, 10.2 Hz, 1H), 6.23 (dd, J=17.1, 1.7 Hz, 1H), 5.73 (dd, J=10.3, 1.7 Hz, 1H), 5.17 (hept, J=6.1 Hz, 1H), 3.90 (s, 3H), 3.61 (t, J=5.6 Hz, 2H), 3.32 (d, J=5.5 Hz, 2H), 2.79 (s, 6H), 2.78 (s, 3H), 2.39 (s, 3H), 1.18 (d, J=6.1 Hz, 6H).

Example 18: N-{2-{[2-(dimethylamino)ethyl](methyl)amino}-6-isopropyloxy-5-{[4-(1-methyl-5,6-difluoro-1H-indol-3-yl)pyrimidin-2-yl]amino}pyridin-3-yl}acrylamide methanesulfonate

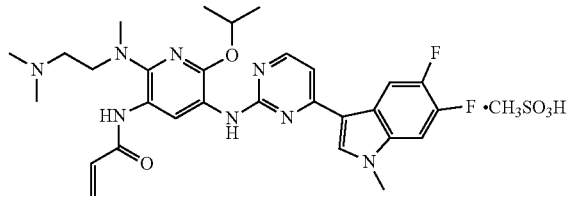

The compound was synthesized in the substantially same manner as those in Example 16. Ethyl acetate was added to the final crude product. The mixture was ultrasonically treated and filtered to produce a product with a yield of 96%.

$^1$H NMR (400 MHz, DMSO-d6) δ 9.99 (s, 2H), 8.82 (s, 1H), 8.26-8.11 (m, 3H), 7.81 (dd, J=10.6, 6.9 Hz, 1B), 7.40 (d, J=6.6 Hz, 1H), 6.82 (dd, J=16.9, 10.3 Hz, 11H), 6.27 (d, J=17.0 Hz, 1H), 5.78 (d, J=10.1 Hz, 1H), 5.25-5.19 (m, 1H), 3.91 (s, 3H), 3.68 (d, J=5.5 Hz, 2H), 3.35 (d, J=5.5 Hz, 2H), 2.86 (s, 3H), 2.82 (s, 3H), 2.80 (s, 3H), 2.36 (s, 3H), 1.21 (d, J=6.1 Hz, 6H).

Example 19: N-{2-{[2-(dimethylamino)ethyl](methy)amino}-6-isopropyloxy-5-{[5-chloro-4-(1-methyl-1H-[pyrro]*pyrrolo*[2,3-b]pyridin-3-yl)pyrimidin-2-yl]amino}pyridin-3-yl}acrylamide

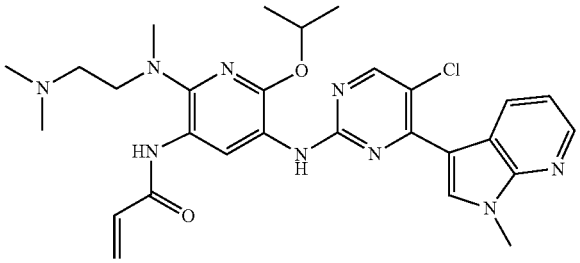

Step 1: Synthesis of $N^2$-methyl-$N^2$-[2-(dimethylamino)ethyl]-6-isopropyloxy-$N^5$-[5-chloro-4-(1-methyl-1H-[pyrro]*pyrrolo*[2,3-b]pyridin-3-yl)pyrimidin-2-yl]-3-nitropyridin-2,5-diamine

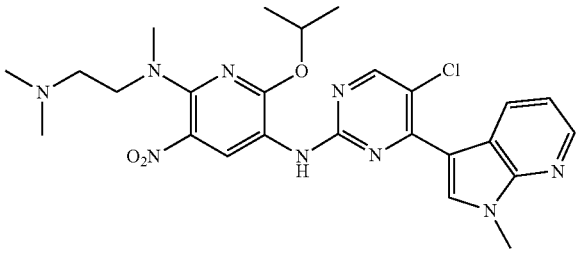

The compound was synthesized in the same manner as those in Step 1 of Example 1 with a yield of 46%. MS m/z: 540.

Step 2: Synthesis of $N^2$-methyl-$N^2$-[2-(dimethylamino)ethyl]-6-isopropyloxy-$N^5$-[5-chloro-4-(1-methyl-1H-[pyrro]*pyrrolo*[2,3-b]pyridin-3-yl)pyrimidin-2-yl]pyridin-2,3,5-triamine

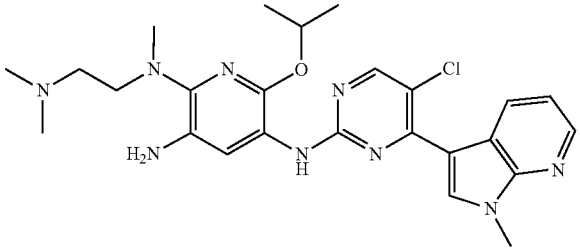

The compound was synthesized in the same manner as those in Step 2 of Example 1 with a yield of 37%. MS m/z: 510 [M+1].

Step 3: Synthesis of N-{2-{[2-(dimethylamino)ethyl](methyl)amino}-6-isopropyloxy-5- {[5-chloro-4-(1-methyl-1H-[pyrro]*pyrrolo*[2,3-b]pyridin-3-yl)pyrimidin-2-yl]amino}pyridin-3-yl}acrylamide

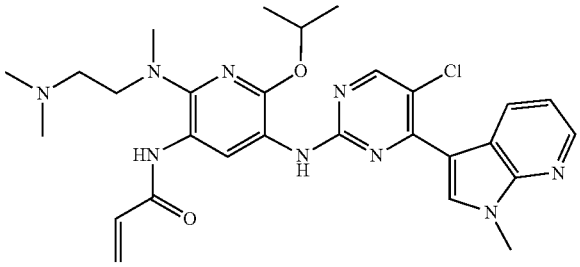

The compound was synthesized in the same manner as those in Step 3 of Example 1 with a yield of 52%. MS m/z: 564 [M+1].

$^1$H NMR (400 MHz, MeOD) δ 8.70 (dd, J=8.0, 1.0 Hz, 1H), 8.61 (s, 1H), 8.41 (s, 1H), 8.40 (s, 1H), 8.29 (dd, J=4.7, 1.5 Hz, 1H), 7.14 (dd, J=8.0, 4.8 Hz, 1H), 6.48 (dd, J=16.9, 2.6 Hz, 1H), 6.42 (dd, J=16.9, 9.2 Hz, 1H), 5.86 (dd, J=9.2, 2.6 Hz, 1H), 5.38-5.32 (m, 1H), 3.97 (s, 3H), 3.74 (t, J=5.7 Hz, 2H), 3.33 (t, J=5.7 Hz, 2H), 2.90 (s, 6H), 2.80 (s, 3H), 1.41 (d, J=6.2 Hz, 6H).

Example 20: N-{2-{[2-(dimethylamino)ethyl](methyl)amino}-6-isopropyloxy-5-{[5-chloro-4-(1-methyl-1H-[pyrro]*pyrrolo*[2,3-b]pyridin-5-yl)pyrimidin-2-yl]amino}pyridin-3-yl}acrylamide

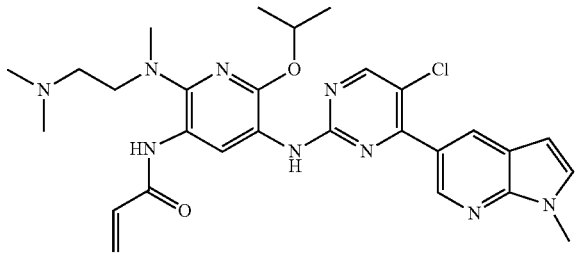

The compound was prepared in the same manner as those in Example 7. MS m/z: 564 [M+1].

$^1$H NMR (400 MHz, $CDCl_3$) δ 9.69 (s, 1H), 9.55 (s, 1H), 8.99 (d, J=1.9 Hz, 1H), 8.71 (s, 1H), 8.50 (s, 1H), 7.52 (s, 1H), 7.24 (d, J=3.5 Hz, 1H), 7.14 (dd, J=16.9, 10.2 Hz, 1H), 6.63 (d, J=3.5 Hz, 1H), 6.54 (dd, J=16.9, 1.9 Hz, 1H), 5.77 (dd, 1=10.2, 1.9 Hz, 1H), 5.26 (hept, J=6.2 Hz, 1H), 3.94 (s, 3H), 3.52 (t, J=5.2 Hz, 2H), 3.11 (t, J=5.2 Hz, 2H), 2.81 (s, 3H), 2.79 (s, 3H), 1.38 (d, 1=6.2 Hz, 6H).

Example 21: N-{2-{[2-(dimethylamino)ethyl](methy)amino}-6-isopropyloxy-5-{[5-chloro-4-(1-methyl-1H-pyrazol-4-yl)pyrimidin-2-yl]amino}pyridin-3-yl}acrylamide

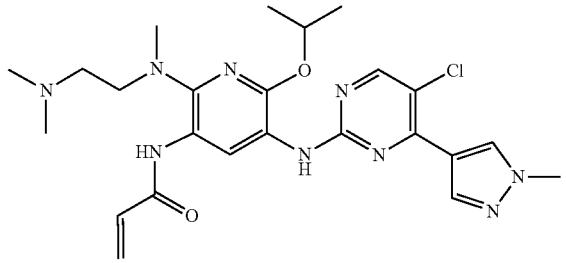

The compound was prepared in the same manner as those in Example 7 with a yield of 8%. MS m/z: 514 [M+1].

$^1$H NMR (400 MHz, $CDCl_3$) δ 9.79 (s, 1H), 9.55 (s, 1H), 9.12 (s, 1H), 8.46 (s, 1H), 8.33 (s, 1H), 7.48 (s, 1H), 6.50 (dd, J=17.0, 2.0 Hz, 1H), 5.77 (dd, J=10.0, 2.0 Hz, 1H), 5.30 5.22 (m, 1H), 4.08 (s, 3H), 3.57 (s, 2H), 3.16 (s, 2H), 2.83 (s, 9H), 1.39 (d, J=6.2 Hz, 6H).

Example 22: N-{2-{[2-(dimethylamino)ethyl](methyl)amino}-6-isopropyloxy-5-{[5-chloro-2'-methoxy-(4,5'-bipyrimidine)-2-yl]amino}pyridin-3-yl}acrylamide

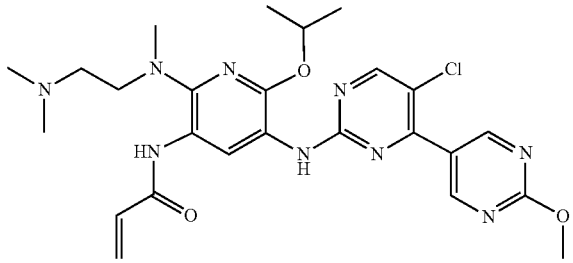

The compound was synthesized in the same manner as those in Example 7.

$^1$H NMR (400 MHz, $CDCl_3$) δ 9.75 (s, 1H), 9.50 (s, 1H), 9.27 (s, 2H), 8.51 (s, 1H), 7.52 (s, 1H), 7.17-7.03 (m, 1H), 6.57 (d, J=16.9 Hz, 1H), 5.76 (d, J=12.0 Hz, 1H), 5.31-5.23 (m, 1H), 4.13 (s, 3H), 3.54 (s, 2H), 3.12 (s, 2H), 2.83 (s, 3H), 2.81 (s, 6H), 1.40 (d, J=6.2 Hz, 6H).

Example 23: N-{2-{[2-(dimethylamino)ethyl](methyl)amino}-6-isopropyloxy-5-{[5-chloro-2'-amino-(4,5'-bipyrimidine)-2-yl]amino}pyridin-3-yl}acrylamide

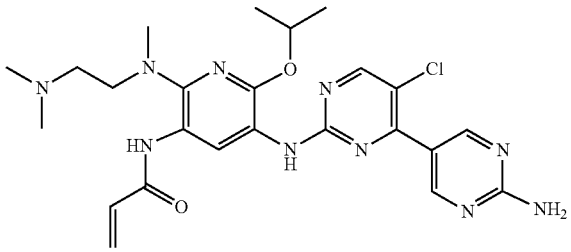

The compound was prepared in the same manner as those in Example 7 with a yield of 8%. MS m/z: 527 [M+1].

$^1$H NMR (400 MHz, $CDCl_3$) δ 9.76 (s, 1H), 9.43 (s, 1H), 9.09 (s, 2H), 8.45 (s, 1H), 7.48 (s, 1H), 7.02 (s, 1H), 6.52 (dd, J=16.9, 1.8 Hz, 1H), 5.75 (dd, J=10.3, 1.8 Hz, IH), 5.61 (s, 2H), 5.26 (hept, J=6.2 Hz, 1H), 3.47 (br s, 2H), 3.05 (br s, 2H), 2.81 (s, 3H), 2.76 (s, 6H), 1.39 (d, J=6.2 Hz, 6H).

II. Examples of the Activity Test of the Present Compounds

Test Example 1: Proliferation Inhibition Effects on Human Skin Cancer Cell (A431, Wild-Type EGFR), Human Lung Cancer Cell (HCC827, EGFR Exon 19 Deletion Activating Mutation), Human Lung Cancer Cell (H1975, EGFR L858R/T790M Resistant Mutation)

Cells in the logarithmic phase were inoculated to 96-well culture plates (cell density: 5000/well, cell suspension: 180 μl/well), and cultured at 37° C. under 5% $CO_2$ for 24 hours. After the culturing, the cells adhered to the well walls. Each of compounds was dissolved in DMSO in advance to formulate a 10 nM stock solution. Upon testing, the stock solution was diluted with complete medium to 10 times the target concentration in another 96-cell plate. And then the compound was added at 20 μl/cell in the 96-well plate in which the cells were inoculated, i.e. the target concentration could be reached. The well for each concentration was triplicated, and the blank control was established. Cells continued to be cultured at 37° C. under 5% $CO_2$ for 72 hours. After the termination of culturing, 50 μl pre-cooled (4° C.) 50% trichloroacetic acid, i.e., TCA was added to each of wells (final concentration=10%), and was placed at 4° C. for 1 hour to fix the cells. The resulting matter was washed with purified water for at least 5 times, and dried naturally in air or at 60° C. in an oven. 4 mg/ml Sulforhodamine B (SRB) solution prepared by 1% glacial acetic acid/purified water was added at 100 μl/well to each well so as to stain for 1 hour at room temperature. The supernatant was discarded. The residue was washed with 1% acetic acid for at least 5 times to remove the non-specifically binding, and dried for use. To each well was added 150 μl of 10 mM Tris-HCl solution for dissolving the contents therein. The OD value was measured at a wavelength of 510 nm, and the inhibition rate was calculated based on the collected data. The result was shown in Table 1.

TABLE 1

| | HCC827 $IC_{50}$ (nM) | H1975 $IC_{50}$ (nM) | A431 $IC_{50}$ (nM) |
|---|---|---|---|
| AZD9291 | 3.80 | 5.43 | 70.43 |
| Example 1 compound | 2.15 | 5.64 | 140.5 |
| Example 2 compound | 4.22 | 5.54 | 195.5 |
| Example 3 compound | 1.34 | 2.28 | 224.2 |
| Example 4 compound | 1.92 | 6.15 | 163.7 |
| Example 5 compound | 2.58 | 4.83 | 181.4 |
| Example 6 compound | 2.36 | 5.20 | 337.8 |
| Example 7 compound | 1.40 | 16.68 | 307.0 |
| Example 8 compound | 5.98 | 8.40 | 375.4 |
| Example 9 compound | 1.17 | 12.58 | 697.2 |
| Example 10 compound | 2.62 | 5.32 | 208.9 |
| Example 11 compound | 2.23 | 7.22 | 210.3 |
| Example 12 compound | 0.96 | 9.01 | 338.6 |
| Example 13 compound | 2.62 | 5.33 | 208.9 |
| Example 14 compound | 0.77 | 5.17 | 241.8 |
| Example 15 compound | 0.69 | 6.28 | 337.4 |
| Example 16 compound | 1.45 | 5.43 | 273.4 |
| Example 17 compound | 5.56 | 7.63 | 375.4 |
| Example 18 compound | 2.24 | 5.07 | 341.3 |
| Example 19 compound | 2.62 | 2.56 | 208.9 |
| Example 20 compound | 8.97 | 42.35 | 800.7 |
| Example 21 compound | 142.4 | 18.55 | 369.8 |
| Example 22 compound | 33.30 | 37.98 | 2765 |
| Example 23 compound | 3.08 | 30.70 | 1145 |

Note:
AZD9291 was prepared according to Example 28 of WO 2013/014448 A1

The test results showed that the compounds of the present invention had a strong proliferation inhibition effect on human lung cancer cell (HCC827, EGFR Exon 19 deletion activating mutation) and human lung cancer cell (H1975, EGFR L858R/T790M resistant mutation), a relatively weak proliferation inhibition effect on human skin cancer cell (A431, wild-type EGFR), that is to say, the compounds of the present invention had a good selectivity.

Test Example 2: Inhibition Effect on the Growth of Subcutaneously Transplanted Tumors of Human Lung Cancer H1975-Bearing Nude Mice The Inhibition effect of the compound of Example 3 of the present invention and AZD9291 on subcutaneously transplanted tumors of human lung cancer H1975-bearing nude mice and the corresponding safety were observed.

Cell cultivation: H1975 was placed in a RPMI-1640 medium containing 10% FBS, and cultivated in a temperature-constant incubator containing 5% $CO_2$ at 37° C. The cells in exponential growth phase were collected and counted for inoculation.

Test animals: 15 BALB/c nude mices, 15 males and 0 female, 6 weeks old, 18-20 g, commercially available from Shanghai Lab. Animal Research Center Three test groups were established: 0.5% sodium carboxymethylcellucose solvent control group, the groups of the compound of Example 3 at 25 mg/kg and the groups of AZD9291 at 25 mg/kg, respectively.

Experimental method: human lung cancer H1975 cell strain ($5\times10^6$/each mouse) was inoculated to nude mice subcutaneously at the right side of the back thereof. Each mouse was inoculated with 0.1 ml, and the tumor growth was observed regularly. After the tumors grew to 100-150 $mm^3$ on average, the mice were divided into groups randomly according to the tumor size and the mouse weight. The compound of Example 3 and AZD9291 were administered by intragastric administration in the dosage of 25 mg/kg, and solvent control groups were administered with equal amount of solvent by intragastric administration, wherein the administration was performed once per day for a continuous period of 12 days. During the entire experimental process, the mouse weight and the tumor size were measured twice per week, so as to observe whether or not the toxic reaction occurs. The tumor volume is calculated as follows:

$$\text{Tumor volume } (mm^3)=0.5\times(\text{Tumor major diameter}\times\text{Tumor minor diameter}^2)$$

Figure 2:
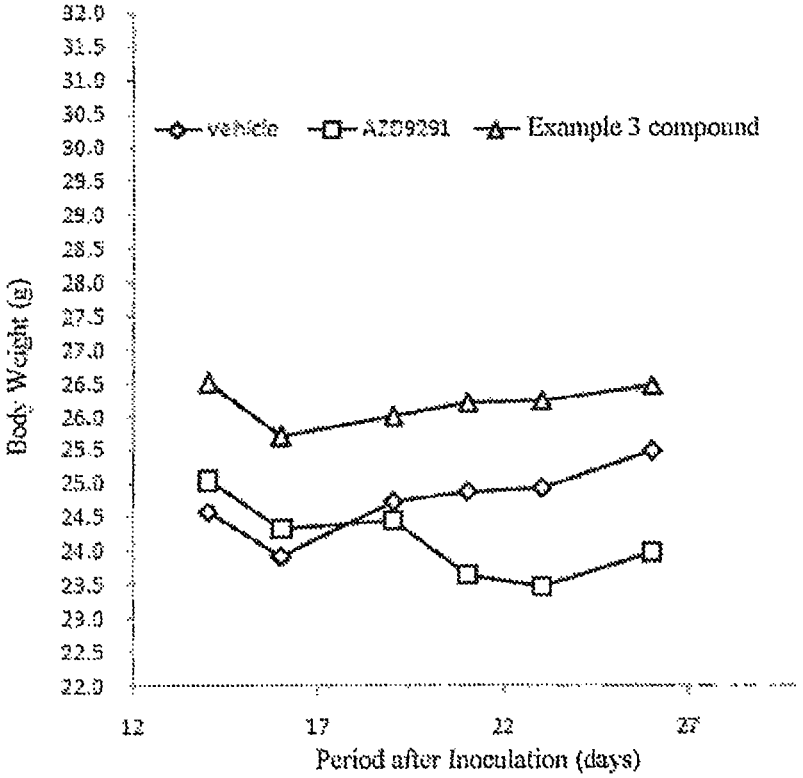
FIG. 2 is the body weight curve for human lung cancer H1975-bearing nude mice at the administration dosage of 25 mg/kg of the compound of Example 3 and AZD9291.

The tumor growth curves of three experimental groups are shown in FIG. 1, and the mice's weight growth curves are shown in FIG. 2. The results show that the compounds of the present invention have a good inhibition effect on the growth of subcutaneously transplanted tumors of human lung cancer H1975-bearing nude mice, while having little effect on the weights of nude mice, and showing a good safety.

All of the literatures mentioned herein are incorporated into the present application by reference. It should be also noted that, upon reading the above mentioned contents of the present application, a person skilled in the art can modify, change or amend the present invention without departing from the spirits of the present invention, and these equivalents are also within the scope as defined by the claims appended in the present application.

What is claimed is:

[1. A compound represented by the following general formula (I), or a pharmaceutically acceptable salt thereof, (I)

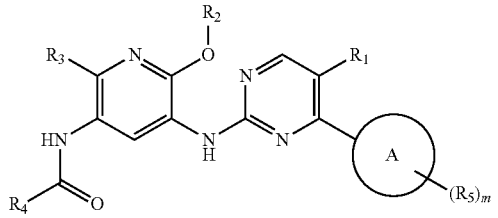

wherein,

Ring A is aryl or heteroaryl;

$R_1$ is selected from a group consisting of hydrogen, halogen, $C_1$-$C_4$alkyl, halo$C_1$-$C_4$alkyl, $C_2$-$_5$alkenyl, $C_2$-$C_6$alkynyl or —CN;

$R_2$ is selected from a group consisting of $C_1$-$C_4$alkyl, halo$C_1$-$C_4$alkyl, $C_2$-$C_6$alkenyl, —$(CH_2)_c OR_7$, —$(CH_2)_q$ $NR_7R_7'$ or —$(CH_2)$ $C(O)R_7$;

$R_4$ is

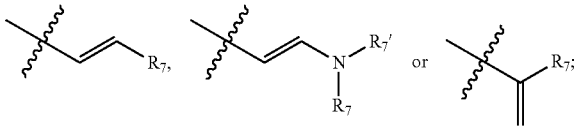

Each $R_5$ is dependently halogen, $C_1$-$C_4$alkyl, halo$C_1$-$C_4$alkyl, $C_2$-$C_6$alkenyl, $C_2$-$C_6$alkynyl, —$OR_6$, —$C(O)R_7$, —$C(O)NR_7R_7'$, —$OR_7$, —$NR_7R_7'$, —CN or —$NO_2$;

$R_3$ is selected from a group consisting of halogen, —CN, —$NO_2$, $C_1$-$C_4$alkyl, halo$C_1$-$C_4$alkyl, —$C(O)R_6$, —$C(O)R_7$, —$C(O)NR_7R_7'$, —$OR_7$, —$OR_6$, —$NHR_7$, —$NR_7$—($C_1$-$C_4$alkyl), —$NR_7$-(halo$C_1$-$C_4$alkyl), —$NR_7(CH_2)_nC(O)R_6$, —$NR_6R_7$, —$NR_7$-heterocycloalkyl, wherein said heterocycloalkyl is unsubstituted or substituted with 1-2 substituents selected from $R_7$, or $—NR_7SO_2R_7$, or heterocycloalkyl that is unsubstituted or substituted with 1-3 substituents selected from halogen, $C_1$-$C_4$alkyl, halo$C_1$-$C_4$alkyl, $—(CH_2)_nOH$, $—NR_7R_7'$, $—OR_7$ or $—C(O)R_7$;

wherein, $R_6$ is $—(CH_2)OR_7$, $—(CH_2)_q(NR_7R_7'$, $—(CH_2)_qNR_7C(O)R_7$, $—(CH_2)_qC(O)R_7$ or $—(CH_2)_qC(O)NR_7R_7'$;

$R_7$ and $R_7'$ are each independently hydrogen, $C_1$-$C_4$alkyl, $C_2$-$C_6$alkenyl, $C_2$-$C_6$alkynyl or halo$C_1$-$C_4$alkyl, or $R_7$, $R_7'$ and the nitrogen atom attached thereto are cyclized together together to form a heterocycloalkyl that is unsubstituted or substituted with 1-3 substituents selected from halogen, $C_1$-$C_4$alkyl, halo$C_1$-$C_4$alkyl, $—(CH_2)_nOH$, $—NR_7R_7'$, $—OR_7$ or $—C(O)R_7$;

m is 1, 2 or 3;

n is 0, 1, 2, 3 or 4;

q is 0, 1, 2, 3 or 4.]

[2. The compound according to claim 1 or a pharmaceutically acceptable salt thereof, wherein Ring A is heteroaryl.]

[3. The compound according to claim 2 or a pharmaceutically acceptable salt thereof, wherein Ring A is indolyl, indazolyl, pyrro[2,3-c]pyridinyl, pyrro[3,2-c]pyridinyl, pyrro[2,3-b]pyridinyl, pyrro[3,2-b]pyridinyl, pyrro[2,3-b]pyrazinyl, indolin-2-onyl, pyridinyl, pyrazolyl or pyrimidinyl.]

[4. The compound according to claim 1 or a pharmaceutically acceptable salt thereof, wherein $R_1$ is hydrogen, halogen or halo$C_1$-$C_4$alkyl.]

[5. The compound according to claim 1 or a pharmaceutically acceptable salt thereof, wherein $R_2$ is $C_1$-$C_4$alkyl or halo$C_1$-$C_4$alkyl.]

[6. The compound according to claim 5 or a pharmaceutically acceptable salt thereof, wherein $R_2$ is $C_2$-$C_4$alkyl or halo$C_2$-$C_4$alkyl.]

[7. The compound according to claim 6 or a pharmaceutically acceptable salt thereof, wherein $R_2$ is isopropyl or trifluoroethyl.]

[8. The compound according to claim 1 or a pharmaceutically acceptable salt thereof, wherein $R_4$ is

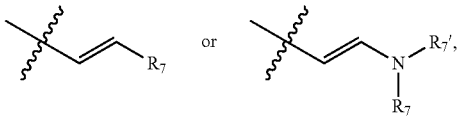

$R_7$ and $R_7'$ are each independently hydrogen or $C_1$-$C_4$alkyl.]

[9. The compound according to claim 8 or a pharmaceutically acceptable salt thereof, wherein $R_4$ is

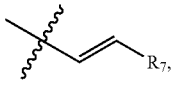

$R_7$ is hydrogen.]

[10. The compound according to claim 1 or a pharmaceutically acceptable salt thereof, wherein $R_3$ is selected from a group consisting of halogen, —CN, $—NO_2$, $C_1$-$C_4$alkyl, halo$C_1$-$C_4$alkyl, $—C(O)R_7$, $—C(O)NR_7R_7'$, $—OR_7$, $—NHR_7$, $—NR_7—(C_1$-$C_4$alkyl), $—NR_7(CH_2)_nC(O)R_6$, or $—NR_6R_7$, or heterocycloalkyl that is unsubstituted or substituted with 1-3 substituents selected from halogen, $C_1$-$C_4$alkyl, halo$C_1$-$C_4$alkyl, $—(CH_2)_nOH$, $—NR_7R_7'$, $—OR_7$ or $—C(O)R_7$;

wherein, $R_6$ is $—(CH_2)OR_7$, $—(CH_2)_qNR_7R_7'$, $—(CH_2)_qC(O)R_7$ or $—(CH_2)_qC(O)NR_7R_7'$;

$R_7$ and $R_7'$ are each independently hydrogen, $C_1$-$C_4$alkyl or halo$C_1$-$C_4$alkyl, or $R_7$, $R_7'$ and the nitrogen atom attached thereto are cyclized together together to form a heterocycloalkyl;

n is 0, 1, 2, 3 or 4;

q is 0, 1, 2, 3 or 4.]

[11. The compound according to claim 10 or a pharmaceutically acceptable salt thereof, wherein $R_3$ is $—NR_6R_7$, in which $R_6$ is $—(CH_2)_qNR_7R_7'$, $R_7$ and $R_7'$ are each independently hydrogen or $C_1$-$C_4$alkyl, q is 2.]

[12. The compound according to claim 10 or a pharmaceutically acceptable salt thereof, wherein $R_3$ is a heterocycloalkyl substituted by one substituent selected from halogen, $C_1$-$C_4$alkyl, halo$C_1C_4$alkyl or $—NR_7R_7'$, $R_7$ and $R_7'$ are each independently hydrogen or $C_1$-$C_4$alkyl.]

[13. The compound according to claim 12 or a pharmaceutically acceptable salt thereof, wherein said heterocycloalkyl is pyrrolidinyl.]

[14. The compound according to claim 1 or a pharmaceutically acceptable salt thereof, wherein each $R_5$ is dependently halogen, $C_1$-$C_4$alkyl, halo$C_1$-$C_4$alkyl, $—OR_7$, $—NR_7R_7'$, —CN or $—N_O$2, $R_7$ and $R_7'$ are each independently hydrogen or $C_1$-$C_4$alkyl, m is 1, 2 or 3.]

[15. The compound according to claim 14 or a pharmaceutically acceptable salt thereof, wherein each $R_5$ is dependently halogen, $C_1$-$C_4$alkyl, $—OR_7$ or $NR_7R_7'$, $R_7$ and $R_7'$ are each independently hydrogen or $C_1$-$C_4$alkyl, m is 1, 2 or 3.]

[16. The compound according to claim 1 or a pharmaceutically acceptable salt thereof, wherein said compound is selected from a group consisting of:

N-{2-{[2-(dimethylamino)ethyl](methyl)amino}-6-isopropyloxy-5-{5-chloro-[4-(1-methyl-1H-indol-3-yl)pyrimidin-2-yl]amino}pyridin-3-yl}acrylamide;

N-{2-{[2-(dimethylamino)ethyl](methyl)amino}-6-isopropyloxy-5-{[4-(1-methyl-1H-indol-3-yl)pyrimidin-2-yl]amino}pyridin-3-yl}acrylamide;

N-{2-{[2-(dimethylamino)ethyl](methyl)amino}-6-(2,2,2-trifluoroethoxyl)-5-{[4-(1-methyl-1H-indol-3-yl)pyrimidin-2-yl]amino)pyridin-3-yl}acrylamide;

N-(2-{[2-(dimethylamino)ethyl](methyl)amino}-6-(2,2,2-trifluoroethoxyl)-5-{5-chloro-[4-(1-methyl-1H-indol-3-yl)pyrimidin-2-yl]amino}pyridin-3-yl}acrylamide;

N-{2-{[2-(dimethylamino)ethyl](methyl)amino}-6-isopropyloxy-5-{[4-(1-methyl-5-fluoro-1H-indol-3-yl)pyrimidin-2-yl]amino}pyridin-3-yl}acrylamide;

N-{2-{[2-(dimethylamino)ethyl](methyl)amino}-6-isopropyloxy-5-{[4-(1-methyl-5,6-difluoro-1H-indol-3-yl)pyrimidin-2-yl]amino}pyridin-3-yl}acrylamide;

N-{2-{[2-(dimethylamino)ethyl](methyl)amino}-6-isopropyloxy-5-{5-chloro[4-(1-methyl-6-fluoro-1H-indol-3-yl)pyrimidin-2-yl]amino}pyridin-3-yl}acrylamide;

N-{2-{[2-(dimethylamino)ethyl](methyl)amino}-6-isopropyloxy-5-{5-chloro[4-(1-methyl-5,6-difluoro-1H-indol-3-yl)pyrimidin-2-yl]amino}pyridin-3-yl}acrylamide;

N-{2-{[2-(dimethylamino)ethyl](methyl)amino}-6-isopropyloxy-5-{5-chloro-[4-(1-methyl-5-fluoro-1H-indol-3-yl)pyrimidin-2-yl]amino}pyridin-3-yl}acrylamide;

N-{2-{[2-(dimethylamino)ethyl](methyl)amino}-6-isopropyloxy-5-{5-fluoro-[4-(1-methyl-5-fluoro-1H-indol-3-yl)pyrimidin-2-yl]amino}pyridin-3-yl}acrylamide;

N-{2-{[2-(dimethylamino)ethyl](methyl)amino}-6-isopropyloxy-5-{5-fluoro-[4-(1-methyl-1H-indol-3-yl)pyrimidin-2-yl]amino}pyridin-3-yl}acrylamide;

N-{2-{[2-(dimethylamino)ethyl](methyl)amino}-6-isopropyloxy-5-{5-fluoro[4-(1-methyl-5,6-difluoro-1H-indol-3-yl)pyrimidin-2-yl]amino}pyridin-3-yl}acrylamide;

N-{2-{[2-(dimethylamino)ethyl](methyl)amino}-6-isopropyloxy-5-{[4-(1-methyl-6-fluoro-1H-indol-3-yl)pyrimidin-2-yl]amino}pyridin-3-yl}acrylamide;

N-{2-{[2-(dimethylamino)ethyl](methyl)amino}-6-(2,2,2-trifluoroethoxyl)-5-{5-fluoro-[4-(1-methyl-1H-indol-3-yl)pyrimidin-2-yl]amino}pyridin-3-yl}acrylamide;

N-{2-{[2-(dimethylamino)ethyl](methyl)amino}-6-(2,2,2-trifluoroethoxyl)-5-{[4-(1-methyl-5-fluoro-1H-indol-3-yl)pyrimidin-2-yl]amino}pyridin-3-yl}acrylamide;

N-{2-{[2-(dimethylamino)ethyl](methyl)amino}-6-isopropyloxy-5-{5-chloro-[4-(1-methyl-1H-indol-3-yl)pyrimidin-2-yl]amino}pyridin-3-yl}acrylamide methanesulfonate;

N-{2-{[2-(dimethylamino)ethyl](methyl)amino}-6-isopropyloxy-5-{5-chloro-[4-(1-methyl-5,6-difluoro-1H-indol-3-yl)pyrimidin-2-yl]amino}pyridin-3-yl}acrylamide methanesulfonate;

N-{2-{[2-(dimethylamino)ethyl](methyl)amino}-6-isopropyloxy-5-{[4-(1-methyl-5,6-difluoro-1H-indol-3-yl)pyrimidin-2-yl]amino}pyridin-3-yl}acrylamide methanesulfonate;

N-{2-{[2-(dimethylamino)ethyl](methyl)amino}-6-isopropyloxy-5-{[5-chloro-4-(1-methyl-1H-pyrro[2,3-b]pyridin-3-yl)pyrimidin-2-yl]amino}pyridin-3-yl}acrylamide;

N-{2-{[2-(dimethylamino)ethyl](methyl)amino}-6-isopropyloxy-5-{[5-chloro-4-(1-methyl-1H-pyrro[2,3-b]pyridin-5-yl)pyrimidin-2-yl]amino}pyridin-3-yl}acrylamide;

N-{2-{[2-(dimethylamino)ethyl](methyl)amino}-6-isopropyloxy-5-{[5-chloro-4-(1-methyl-1H-pyrazol-4-yl)pyrimidin-2-yl]amino}pyridin-3-yl}acrylamide;

N-{2-{[2-(dimethylamino)ethyl](methy)amino}-6-isopropyloxy-5-{[5-choro-2'-methoxy-(4,5'-bipyrimidine)-2-yl]amino}pyridin-3-yl}acrylamide; and N-{2-{[2-(dimethylamino)ethyl](methyl)amino}-6-isopropyloxy-5-{[5-chloro-2'amino-(4,5'-bipyrimidine)-2-yl]amino}pyridin-3-yl}acrylamide.]

[17. A process for preparing the compound represented by the general formula (I) of claim 1, comprising the steps of:

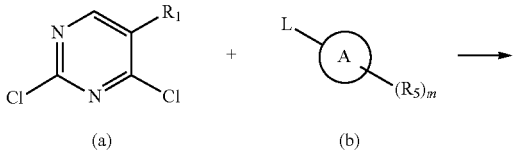

(a) (b)

-continued

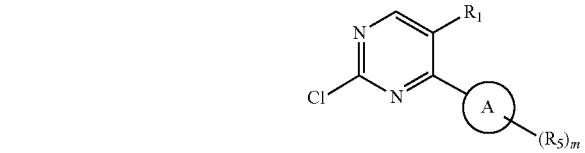

Intermediate 2

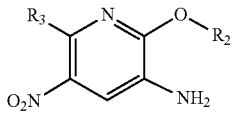

Intermediate 1

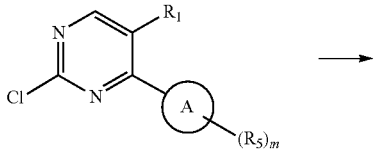

Intermediate 2

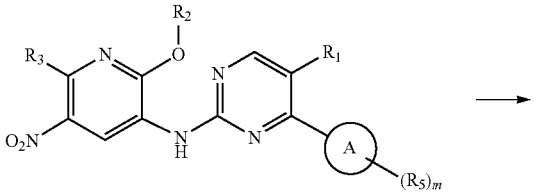

(c)

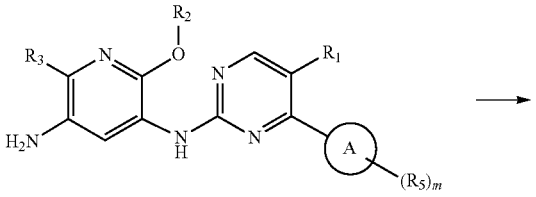

(d)

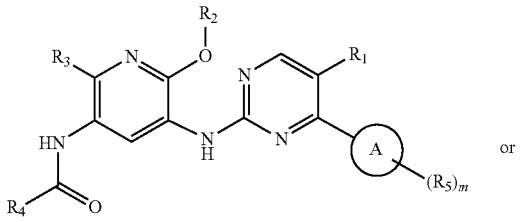

or (I)

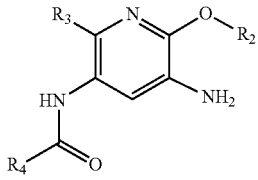

Intermediate 1′

-continued

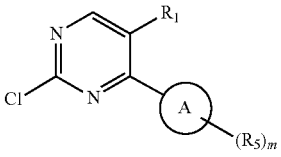

Intermediate 2

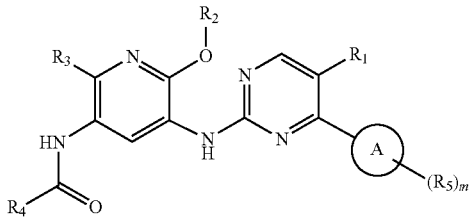

(I)

wherein ring A, $R_1$, $R_2$, $R_3$, $R_4$, $R_5$ and m are defined as in claim 1; L represents a leaving group, including hydrogen, halogen or

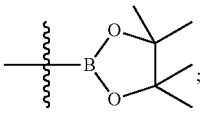

compounds (a) and (b) are used as starting material, and subjected to substitution under the catalysts to produce an Intermediate 2; the Intermediate 2 and an Intermediate 1 are subjected to substitution or coupling reaction to produce a compound (c), the nitro group of the compound (c) is reduced to produce a compound (d), the compound (d) is acylated to produce a compound (I); or the Intermediate 2 and an Intermediate 1' are subjected to substitution or coupling reaction to directly produce a compound (I).]

[18. A pharmaceutical composition, comprising the compound represented by formula (I) of claim 1 or a pharmaceutically acceptable salt thereof and a pharmaceutically acceptable carrier, excipient or diluent.]

[19. A method for treating an EGFR activating or resistant mutation mediated lung cancer in a mammal, said method comprises administering to a mammal the compound represented by formula (I) of claim 1 or a pharmaceutically acceptable salt thereof, or a pharmaceutical composition comprising a therapeutically effective amount of a compound represented by formula (I) of claim 1 and a pharmaor ceutically acceptable carrier, excipient or diluent.]

[20. A method for selectively inhibiting an EGFR activating or resistant mutation over a EGFR, said method comprises contacting a biological sample with or administering to a lung cancer patient the compound represented by formula (I) of claim 1 or a pharmaceutically acceptable salt thereof or a pharmaceutical composition containing the same.]

[21. The method of claim 19, wherein the mammal is a human.]

*22. A pharmaceutical composition comprising a compound having the structure:*

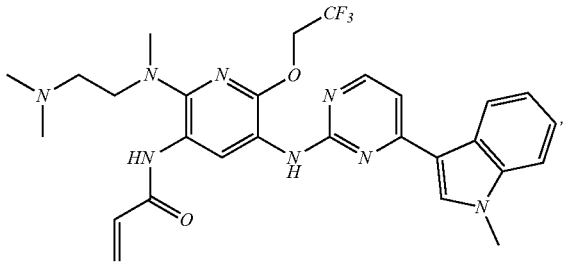

*and a pharmaceutically acceptable carrier, excipient or diluent.*

*23. A pharmaceutical composition comprising a compound having the structure:*

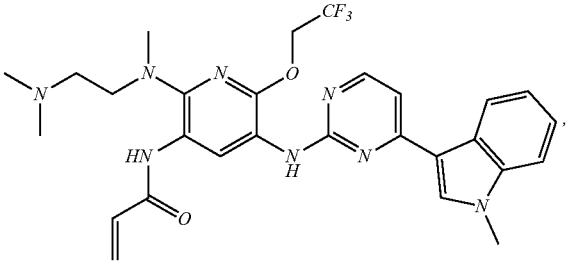

*or a pharmaceutical salt thereof and a pharmaceutically acceptable carrier, excipient or diluent.*

*24. A method for treating an EGFR activating or resistant mutation-mediated lung cancer in a mammal, said method comprises administering to the mammal a compound having the structure:*

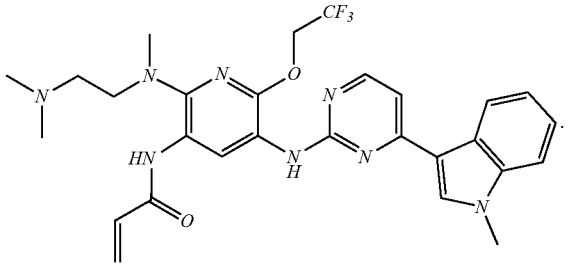

*25. A method for treating an EGFR activating or resistant mutation-mediated lung cancer in a mammal, said method comprises administering to the mammal a compound having the structure:*

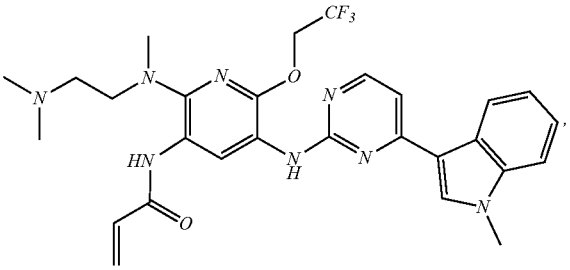

*or a pharmaceutical salt thereof.*

* * * * *